(12) United States Patent
Van Nieuwenhze et al.

(10) Patent No.: US 9,518,088 B2
(45) Date of Patent: Dec. 13, 2016

(54) PEPTIDE-PHOSPHOLIPID CONJUGATES

(75) Inventors: Michael S. Van Nieuwenhze, Bloomington, IN (US); William W. Turner, Bloomington, IN (US); Joseph L. Witztum, San Diego, CA (US); Karsten Hartvigsen, Copenhagen (DK)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 13/983,435

(22) PCT Filed: Jan. 19, 2012

(86) PCT No.: PCT/US2012/021819
§ 371 (c)(1),
(2), (4) Date: Sep. 10, 2013

(87) PCT Pub. No.: WO2012/108990
PCT Pub. Date: Aug. 16, 2012

(65) Prior Publication Data
US 2013/0345117 A1 Dec. 26, 2013

Related U.S. Application Data

(60) Provisional application No. 61/440,231, filed on Feb. 7, 2011.

(51) Int. Cl.
| | | |
|---|---|---|
| *A61K 38/00* | (2006.01) | |
| *A61P 9/10* | (2006.01) | |
| *C07K 14/47* | (2006.01) | |
| *C07K 7/08* | (2006.01) | |
| *A61K 47/48* | (2006.01) | |
| *C07K 5/083* | (2006.01) | |
| *C07K 5/103* | (2006.01) | |
| *C07K 7/06* | (2006.01) | |

(52) U.S. Cl.
CPC ........... *C07K 7/08* (2013.01); *A61K 47/48053* (2013.01); *C07K 5/0806* (2013.01); *C07K 5/1008* (2013.01); *C07K 7/06* (2013.01)

(58) Field of Classification Search
CPC .............................. A61K 38/00; A61K 39/0012
See application file for complete search history.

(56) References Cited

U.S. PATENT DOCUMENTS 6,664,230 B1 * 12/2003 Fogelman et al. ............. 514/1.9

OTHER PUBLICATIONS

Boullier, A. et al. Phosphocholine as a pattern recognition ligand for CD36, J. Lipid Res. 46:969-976 (2005).
Boullier, A. et al. Phosphorylcholine as a pattern recognition ligand for CD36, FASEB J., 19:Suppl. S, Part 1, 222.13, (2005), Abstract No. A285, [Experimental Biology 2005 Meeting/35th International Congress of Physiological Sciences; San Diego, CA, USA; Mar. 31-Apr. 6, 2005].
Friedman P et al. Correlation of Antiphospholipid Antibody Recognition with the Structure of Synthetic Oxidized Phospholipids, J. Biol. Chem. 277:7010-7020 (2002).
Friedman P. et al. Phosphorylcholine-structural necessity of oxidized phospholipids for CD36 binding, Chem. Phys. Lipids. 130:35, Abtract No. SO 16, (2004) [45th International Conference on the Bioscience of Lipids; Ioannina, Greece; May 25-29, 2004].
Olivier, K. Synthesis of biologically active peptides: I. Synthesis of a model of scavenger receptor ligands in oxidized low-density lipoprotein. II. Progress toward the total synthesis of the antibacterial glycopeptide mannopeptimycin (Ph. D. Thesis), Dec. 8, 2010, [UMI dissertation publishing, Proquest, Ann Arbor, MI, USA].

(Continued)

*Primary Examiner* — Hasan Ahmed
*Assistant Examiner* — Kaipeen Yang
(74) *Attorney, Agent, or Firm* — Klintworth & Rozenblat IP LLC

(57) ABSTRACT

The present invention provides a peptide-phospholipid conjugate of Formula 1:

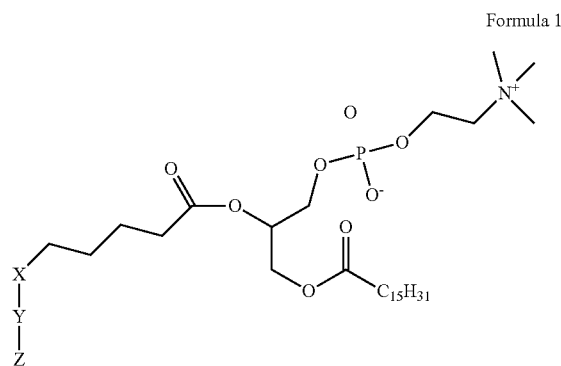

Formula 1 wherein: X is selected from the group consisting of —$CR^1R^2$—, —$R^3$—, —O—, —S—, and —$S^+(R^3)$—; Y is selected from the group consisting of a bond, alkyl, alkenyl, alkynyl, haloalkyl, alkoxyalkyl, hydroxyalkyl, amino, ether, cycloamino, cycloether, aryl heteroaryl, arylalkyl, heteroarylalkyl, hydroxyaryl, arylether, cycloalkyl, heterocycloalkyl, hydroxycycloalkyl, halocycloalkyl, and aminocycloalkyl; Z is a peptide comprising 1 to 50 amino acids; $R^1$ and $R^2$ each independently selected from the group consisting of hydrogen, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl; and $R^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

20 Claims, 15 Drawing Sheets

(56) References Cited

OTHER PUBLICATIONS

Onyango, A.N. et al. Reactions of 1-stearoyl-2-(13'-oxo-9',11'-tridecadienoy I)-sn-glycero-3-phosphocholine with amino acids and peptides and its differential generation from hydroperoxides of 1-stearoyl-2-.alpha.-linolenoyl-sn-glycero-3-phosphocholine and 1-stearoyl-2-linoleoyl-sn-glycero-3-phosph ocholine, Bull. Chem. Soc. Ethiop. 22:269-276 (2008).
Rosseto R. et al. A rapid and efficient method for migration-free acylation of lysophospholipids: synthesis of phosphatidylcholines with sn-2-chain-terminal reporter groups, Tetrahedron Letters 46:2941-2944 (2005).
Steinberg, D. et al. Beyond Cholesterol. Modifications of Low-Density Lipoprotein that Increase its Atherogenicity, N. Engl. J. Med. 320:915-924 (1989).
Witztum, J.L. et al. Role of Oxidized Low Density Lipoprotein in Atherogenesis, J. Clin. Invest. 88:1785-1792 (1991).
Krieger, M. The Other Side of Scavenger Receptors: Pattern Recognition for Host Defense, Curr. Opin. Lipidol. 8:275-280 (1997).
Sawamura, T. et al. An Endothelial Receptor for Oxidized Low-Density Lipoprotein, Nature 386:73-77 (1997).
Steinberg, D. Low Density Lipoprotein Oxidation and its Pathobiological Significance, J. Biol. Chem. 272: 20963-20966 (1997).
Yamada, Y. et al. Scavenger Receptor Family Proteins. Roles for Atherosclerosis, Host Defense, and Disorders of the Central Nervous System, Cell. Mol. Life Sci. 54:628-640 (1998).
Endemann, G. et al. CD36 is a Receptor for Oxidized Low Density Lipoprotein, J. Biol. Chem. 268:11811-11816 (1993).
McIntyre, T.M. et al. Biologically Active Oxidized Phospholipids, J. Biol. Chem. 274: 25189-25192 (1999).
Witztum, J.L. et al. Oxidized Phospholipids and Isoprostanes in Atherosclerosis, Curr. Opin. Lipidol. 9:441-448 (1998).
Gillotte, K.L et al. Oxidized Phospholipids, Linked to Apolipoprotein B of Oxidized LDL, are Ligands for Macrophage Scavenger Receptors, J. Lipid Res. 41:824-833 (2000).
Kamido, H. et al. Identification of Core Aldehydes Among in Vitro Peroxidation Products of Cholesteryl Esters, Lipids 28:331-336 (1993).
Kamido, H. et al. Lipid Ester-Bound Aldehydes among Copper-Catalyzed Peroxidation Products of Human Plasma Lipoproteins, J. Lipid Res. 36:1876-1886 (1995).
Boullier, A. et al. The Binding of Oxidized Low Density Lipoprotein to Mouse CD36 is Mediated in Part by Oxidized Phospholipids That are Associated with Both the Lipid and Protein Moieties of the Lipoprotein, J. Biol. Chem. 275:9163-9169 (2000).
Podrez, E.A. et al. A Novel Family of Atherogenic Oxidized Phospholipids Promotes Macrophage Foam Cell Formation via the Scavenger Receptor CD36 and Is Enriched in Atherosclerotic Lesions, J. Biol. Chem. 277:38517-38523 (2002).
Podrez, E.A. et al. Identification of a Novel Family of Oxidized Phospholipids That Serve as Ligands for the Macrophage Scavenger Receptor CD36, J. Biol. Chem. 277:38503-38516 (2002).
Horkko, S. et al. Monoclonal Autoantibodies Specific for Oxidized Phospholipids or Oxidized Phospholipid-Protein Adducts Inhibit Macrophage Uptake of Oxidized Low-Density Lipoproteins, J. Clin. Invest. 103:117-128 (1999).
Binder, C.J. et al. Pneumococcal Vaccination Decreases Atherosclerotic Lesion Formation: Molecular Mimicry Between *Streptococcus pneumoniae* and Oxidized LDL, Nat. Med. 9:736-743 (2003).
Chou, M.-Y. et al. Oxidation-Specific Epitopes are Dominant Targets of Innate Natural Antibodies in Mice and Humans. J. Clin. Invest. 119:1335-1349 (2009).
Fields, C.G. et al. HBTU Activation for Automated Fmoc Solid-Phase Peptide Synthesis, Pept. Res. 4:95-101 (1991).
International Searching Authority, International Search Report and Written Opinion for PCT/US2012/021819 dated Aug. 28, 2012, 13 pages.

\* cited by examiner

PEPTIDE-PHOSPHOLIPID CONJUGATES

CROSS-REFERENCE TO RELATED APPLICATIONS

The present application is the National Stage of International Application No. PCT/US2012/021819, filed Jan. 19, 2012, which claims the benefit of U.S. Provisional Patent Application No. 61/440,231 filed Feb. 7, 2011. The content of the U.S. Provisional Patent Application is hereby incorporated by reference in its entirety.

STATEMENT REGARDING FEDERALLY SPONSORED RESEARCH OR DEVELOPMENT

This invention was made with government support under GM069338 and HL086559 awarded by the National Institutes of Health. The Government has certain rights in the invention.

BACKGROUND OF THE INVENTION

Oxidized low-density lipoprotein (OxLDL) is believed to play an important role in the pathogenesis of atherosclerosis.[1] Unregulated uptake of OxLDL by macrophages within the arterial wall leads to foam cell formation followed by development of the fatty streak that is typical of early atherosclerotic lesions.[1,2] Macrophages express a number of scavenger receptors that bind OxLDL.[3-6] Among these is CD36[7] which recent evidence suggests may be an important scavenger receptor involved in the uptake of OxLDL by macrophages and may have a significant role in foam cell formation in vivo. The epitope(s) responsible for recognition of OxLDL by CD36, and other scavenger receptors, have not been clearly defined. Identification of the structural features on OxLDL that are responsible for recognition by CD36 could provide a template for the design of compounds with highly specific interactions with these macrophages and other immune system components with the eventual goal of finding new strategies for the treatment of atherosclerosis.

A wide variety of biologically active phospholipid oxidation products can be formed upon oxidation of LDL.[8,9] For example, oxidation of the phospholipid 1-palmitoyl-2-arachidonyl-sn-glycero-3-phosphorylcholine (PAPC, 1) yields an oxidized phospholipid by-product, 1-palmitoyl-2-(5'-oxo)valeroyl-sn-glycero-3-phosphoryl-choline (POVPC, 2), with a reactive aldehyde at the ε-carbon (Scheme 1).

Scheme 1. Biological oxidation of PAPC leading to the fragment POVPC.

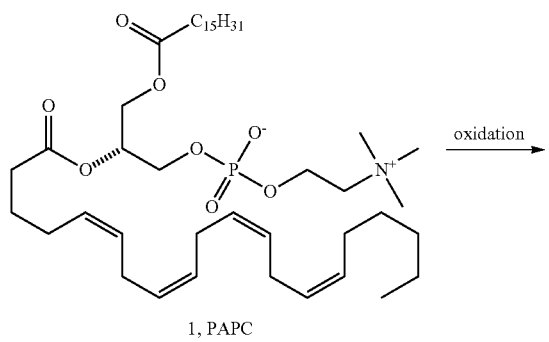

1, PAPC

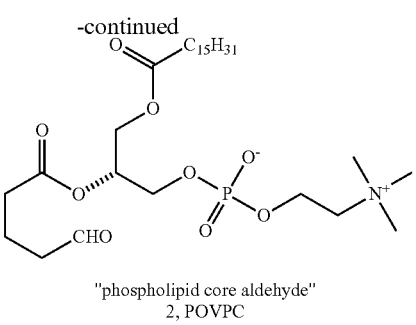

"phospholipid core aldehyde"
2, POVPC

This reactive "phospholipid core aldehyde" in turn forms adducts with lysine residues of apoB, or other proteins, as well as other amine-containing phospholipids.[10-12]

Previous work has shown that binding of OxLDL to CD36 is mediated by oxidized phospholipids (OxPLs).[13-15] In addition, a natural autoantibody against OxLDL, designated E06, was isolated from hypercholesteremic apolipoprotein E (apoE)-deficient mice and was shown to block the uptake of OxLDL by macrophages.[16] Detailed studies of POVPC and variously modified conjugates revealed that the phosphorylcholine head group is essential for binding to CD36 and for antigenicity for E06, but that this activity required prior conjugation of the sn-2 aldehyde with a peptide or protein to yield a Schiff's base.[17,18] Initial experiments demonstrated that Schiff's base conjugates of POVPC with bovine serum albumin (BSA) inhibited binding of OxLDL to CD36. As illustrated in FIG. 1A, a POVPC conjugate with a short peptide chain containing a single lysine residue for imine formation also inhibited binding.

The aqueous solution of the conjugate slowly lost its activity in the assay as the imine hydrolyzed. In an effort to improve the aqueous stability of the Schiff's base conjugate, the imine intermediate was reduced to the corresponding amine with sodium cyanoborohydride. This compound retained its competitive binding activity but was still prone to a slow decomposition in aqueous solution, presumably from intramolecular O'N-acyl transfer, as illustrated in FIG. 1B.

There is therefore a need for a stable compound with high selectivity for these specific antibodies and macrophage receptors that could be used for the treatment of atherosclerosis. Instability of both the imine and amine adducts means that the compounds generated to this point do not meet this goal.

SUMMARY OF THE INVENTION

The present invention is defined by the appended claims and statements within this summary should not be taken as limitations on those claims.

In one aspect, the present invention provides peptide-phospholipid conjugates of Formula 1.

In another aspect, the present invention provides a method of manufacturing a peptide-phospholipid conjugate of Formula 2.

In a further aspect, the present invention provides a pharmaceutical formulation for treating or preventing atherosclerosis, the formulation comprising: a peptide-phospholipid conjugate of Formula 1 or a pharmaceutically acceptable salt, prodrug, salt of a prodrug, or a combination thereof, and a pharmaceutically acceptable excipient.

DEFINITIONS

Figure 1A:
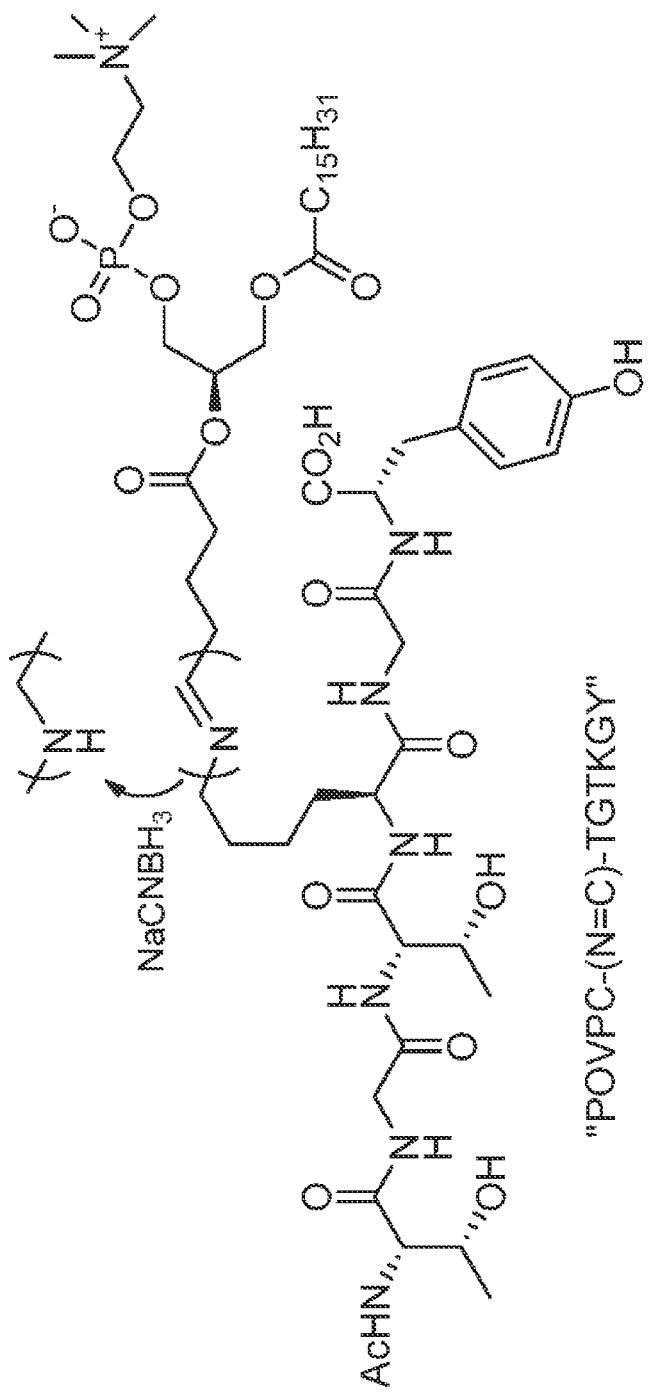
FIG. 1A illustrates POVPC adducts and their reduction to amines.
Figure 1B:
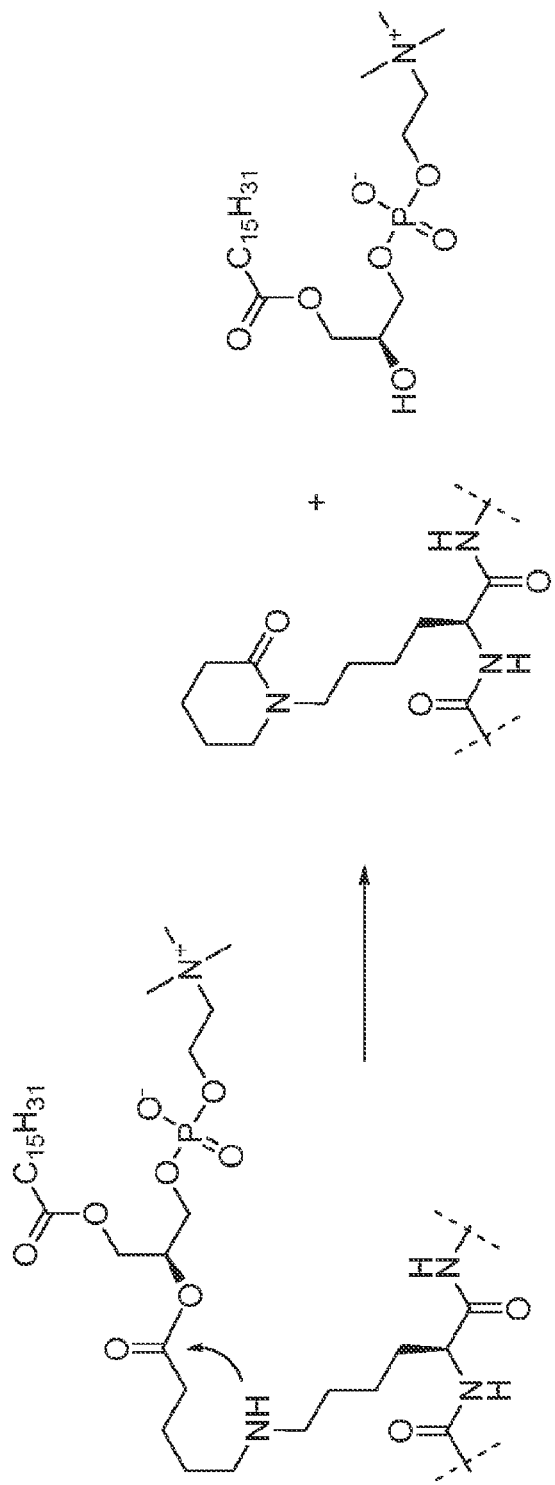
FIG. 1B illustrates a proposed mechanism for intramolecular decomposition of the amines of FIG. 1A.

As used herein, the term "POVPC" refers to 1-palmitoyl-2-oxovaleroyl-sn-glycero-3-phosphorylcholine.

As used herein, the term "amino acid" refers to molecules containing an amine group, a carboxylic acid group and a side chain that varies between different amino acids. Example amino acids include α-amino acids, where the amino group is attached to the carbon atom immediately adjacent to the carboxylate group (the α-carbon).

As used herein, the term "proteinogenic amino acid" refers to amino acids found in eukaryotes, for example L-alanine, L-cysteine, L-selenocysteine, L-aspartic acid, L-glutamic acid, L-phenylalanine, glycine, L-histidine, L-isoleucine, L-lysine, L-leucine, L-methionine, L-asparagine, L-proline, L-glutamine, L-arginine, L-serine, L-threonine, L-valine, L-tryptophan, and L-tyrosine.

As used herein, the term "peptide" refers to molecules comprising one or more amino acids, wherein each amino acid is preferably linked to at least one other amino acid by a peptide bond.

As used herein, the term "treatment" includes the alleviation, amelioration or control of a pathology, disease, disorder, process, condition or event. In this context, the term "treatment" is further to be understood as embracing use to reverse, restrict or control progression of any specified pathology, disease, disorder, process, condition, or event. If any pathology, disease, disorder, process, condition or event is associated with pain, the term "treatment" preferably encompasses the alleviation, amelioration or control (including temporal or permanent removal) of at least one further sequela or symptom in addition to pain, such as inflammation, cough, effusion, and more preferably of all symptoms and most preferably of the total clinical picture of the respective pathology, disease, disorder, process, condition or event.

As used herein, the term "lower alkyl" refers to an alkyl moiety containing from 1 to 6 carbon atoms, and may be straight-chain or branched. These moieties include, but are not limited to, methyl, ethyl, propyl, isopropyl, butyl, isobutyl, tertiary butyl, amyl, and hexyl.

DETAILED DESCRIPTION

The present invention is based on the discovery of novel peptide-phospholipid conjugates based on POVPC. The peptide-phospholipid conjugates of the invention are stable, have strong, specific binding with the CD36 macrophage receptor, and are soluble in aqueous media. The conjugates have also been shown to efficiently compete for binding of OxLDL to macrophages, and may therefore be used in the treatment and prevention of atherosclerosis.

In a first aspect, the present invention provides peptide-phospholipid conjugates of Formula 1:

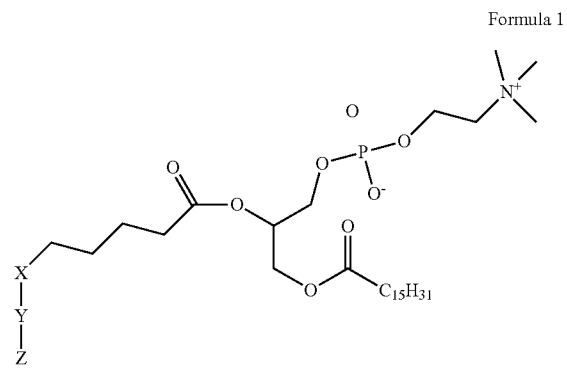

Formula 1

Wherein moiety X is selected from the group consisting of —$CR^1R^2$—, —$NR^3$—, —O—, —S—, and —$S^+(R^3)$—. Moiety Y is a linker between moiety X and peptide Z, and is preferably selected from the group consisting of a bond, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Moiety Z is a peptide preferably comprising 1 to 50 amino adds. $R^1$ and $R^2$ are each independently selected from the group consisting of hydrogen, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and $R^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

Preferably, moiety X is selected from the group consisting of —O— and —$NR^3$—. More preferably, X is an —$NR^3$— group, wherein $R^3$ is selected from the group consisting of alkyl, haloalkyl, alkoxyalkyl, hydroxyalkyl, and aminoalkyl. Yet more preferably, $R^3$ is alkyl. Still more preferably, $R^3$ is lower alkyl. Without being bound to any particular theory, it is believed that the tertiary nature of the nitrogen atom in the —$NR^3$— group prevents the decomposition of the conjugate from intramolecular O'N-acyl transfer. Moiety Y is preferably selected from the group consisting of a bond, alkyl, alkenyl, alkynyl, haloalkyl, alkoxyalkyl, and hydroxyalkyl. More preferably, Y is selected from the group consisting of a bond and alkyl. Most preferably, Y is a bond.

Preferably, peptide Z comprises 1 to 25 amino acids. More preferably, Z comprises 1 to 15 amino acids. As illustrated in the examples below, conjugates bearing peptide moieties differing in size and/or composition exhibit similar biological activity. Without being bound to any, particular theory, this is believed to be due to the fact that the binding to the CD36 macrophage receptor is driven mainly by the phospholipid portion of the conjugates, while the main function of peptide Z is to endow the conjugate with sufficient solubility in aqueous media. Accordingly, the specific identity of each of the amino acids in the peptide Z is not crucial, nor is the size of the peptide. Rather, the requirement is that a sufficient number of amino acids enhancing the water solubility of a given peptide-phospholipid conjugate are included.

As a consequence, the invention is not limited to peptides specifically disclosed herein, as one of ordinary skill in the art can readily prepare water-soluble conjugates by including appropriate amino acids in the peptide that insure sufficient solubility in aqueous media. Preferably, a peptide-phospholipid conjugate should have a solubility of at least 100 µM in aqueous media. More preferably, the solubility should be of at least 200 µM, and, most preferably, of at least 300 µM.

Preferred amino acids include proteinogenic amino acids. More preferred amino acids include those enhancing or at least not diminishing the water solubility of the peptide-phospholipid conjugates, such as α-amino acids bearing polar or electrically charged moieties in their side chains. Among proteinogenic amino acids, more preferred are arginine, histidine, lysine, aspartic acid, glutamic acid, serine, threonine, asparagine, glutamine, and glycine. Also, in the peptide a number of amino acid residues may be modified or replaced, as needed.

The peptide portion of a peptide-phospholipid conjugate may be synthesized by methods known to those of ordinary skill in the art, for example by standard Fmoc solid phase peptide synthesis.[21] The peptide may then be attached to lyso-PC via a linker of formula —CH$_2$CH$_2$CH$_2$C(O)OH, for example by attaching the linker to an amino acid side chain of the peptide and bonding the carboxylic acid moiety of the linker to lyso-PC. In embodiments where the peptide includes a lysine residue, the present invention provides a method for synthesizing peptide-phospholipid conjugates of Formula 2:

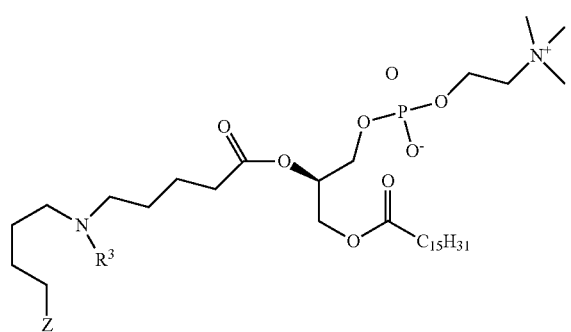

Formula 2

The method involves a reaction forming an ester bond between the acid of Formula 3 and the hydroxyl group of lyso-PC:

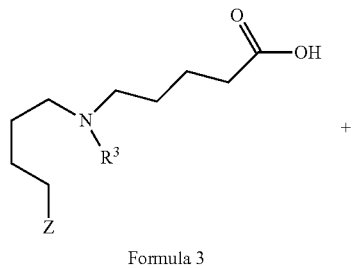

Formula 3

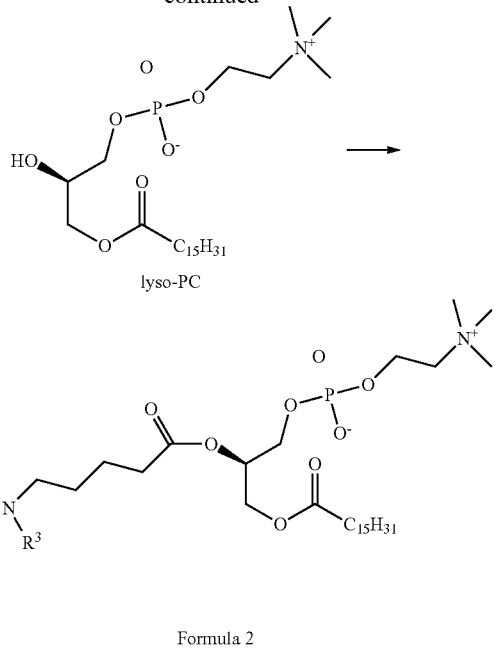

lyso-PC

Formula 2

The formation of the bond may be speeded up by a coupling reagent, for instance a carbodiimide such as dicyclohexylcarbodiimide or diisopropylcarbodiimide. Suitable solvents for the reaction include, but are not limited to, CHCl$_3$, CH$_2$Cl$_2$, tetrahydrofuran, acetonitrile, and dimethylformamide.

Formulas 2 and 3, R$^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Preferably, R$^3$ is selected from the group consisting of alkyl, haloalkyl, alkoxyalkyl, hydroxyalkyl, and aminoalkyl. More preferably, R$^3$ is alkyl. Yet more preferably, R$^3$ is lower alkyl.

Z is a peptide comprising 1 to 50 amino acids. More preferably, Z is a peptide comprises 1 to 25 amino acids. Most preferably, Z comprises 1 to 15 amino acids. The acid of Formula 3 may be synthesized by functionalizing the side chain of a lysine side chain of peptide Z, for example by the double alkylation of the first step of the synthetic scheme of FIG. 2.

Product peptide-phospholipid conjugates may be purified to homogeneity via high-performance liquid chromatography (HPLC) using normal, reverse-phase or other stationary phases as needed. Preferably, each product should be subjected to thorough spectroscopic characterization, for example through $^1$H and $^{13}$C NMR, and/or high-resolution MS, to insure the purity and identity of the product peptide-phospholipid conjugate.

The peptide-phospholipid conjugates of the invention may be used in the development of treatments for the prevention of atherosclerosis. Without being bound to any particular theory, it is believed that their affinity for the CD36 macrophage receptor may provide a template for the design of compounds and formulations that promote the deactivation and clearance of OxLDL.

Accordingly, in a further aspect, the present invention provides a pharmaceutical formulation for treating or preventing atherosclerosis, the formulation comprising: a peptide-phospholipid conjugate of Formula 1 or a pharmaceutically acceptable salt, prodrug, salt of a prodrug, or a combination thereof, and a pharmaceutically acceptable excipient:

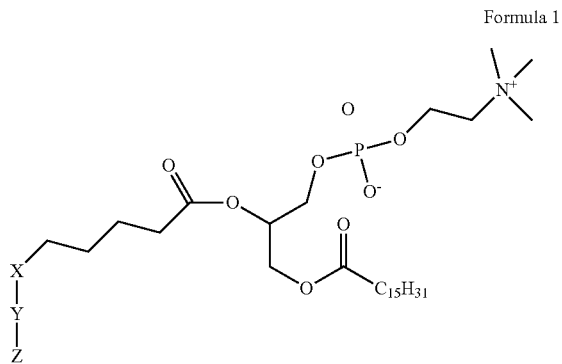

Formula 1

Wherein moiety X is preferably selected from the group consisting of $CR^1R^2—$, $—NR^3—$, $—O—$, $—S—$, and $—S^+(R^3)—$. Moiety Y is a linker between moiety X and peptide Z, and is preferably selected from the group consisting of a bond, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl. Moiety Z is a peptide preferably comprising 1 to 50 amino acids. $R^1$ and $R^2$ are each independently selected from the group consisting of hydrogen, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl, and $R^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

Preferably, moiety X is selected from the group consisting of $—O—$ and $—NR^3—$. More preferably, moiety X is an $—NR^3—$ group, wherein $R^3$ is selected from the group consisting of alkyl, haloalkyl, alkoxyalkyl, hydroxyalkyl, and aminoalkyl. Yet more preferably, $R^3$ is alkyl. Still more preferably, $R^3$ is lower alkyl. Moiety Y is preferably selected from the group consisting of a bond, alkyl, alkenyl, alkynyl, haloalkyl, alkoxyalkyl, and hydroxyalkyl. More preferably, Y is selected from the group consisting of a bond and alkyl. Most preferably, Y is a bond. Preferably, peptide Z is a peptide comprises 1 to 25 amino acids. More preferably, Z comprises 1 to 15 amino acids.

The invention also provides a method for the treatment or prevention of atherosclerosis comprising administering to a mammal a formulation as defined above. Various formulations of one or more peptide-phospholipid conjugates may be used for administration to an individual in need thereof. In some aspects, one or more peptide-phospholipid conjugates may be administered neat. In other aspects, various formulations of peptide-phospholipid conjugates and a pharmaceutically acceptable excipient(s) can be administered. Pharmaceutically acceptable excipients are known in the art. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington. The Science and Practice of Pharmacy 20th Ed. Mack Publishing (2000).

In some embodiments, peptide-phospholipid conjugates may be formulated for administration by injection (e.g., intraperitoneally, intravenously, subcutaneously, intramuscularly, etc.), although other forms of administration (e.g., oral, mucosal, via inhalation, sublingually, etc.) can be also used. Accordingly, peptide-phospholipid conjugates and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 μg/kg body weight; at least about 500 μg/kg body weight; at least about 250 μg/kg body weight; at least about 100 μg/kg body weight; at least about 50 μg/kg body weight; at least about 10 μg/kg body weight; at least about 1 μg/kg body weight, or less, is administered. For repeated administrations over several days or longer, depending on the condition, the treatment is sustained until a desired suppression of disease symptoms occurs. An exemplary dosing regimen comprises administering an initial dose of about 2 mg/kg, followed by a weekly maintenance dose of about 1 mg/kg of the peptide-phospholipid conjugate or followed by a maintenance dose of about 1 mg/kg every other week. However, other dosage regimens may be useful, depending on the pattern of pharmacokinetic decay that the practitioner wishes to achieve. Empirical considerations, such as the half-life, will contribute to determination of the dosage. The progress of this treatment is easily monitored by conventional techniques and assays.

In some individuals, more than one dose may be required. Frequency of administration may be determined and adjusted over the course of treatment. For example, frequency of administration may be determined or adjusted based on the type and severity of the atherosclerosis to be treated, whether the agent is administered for preventive or therapeutic purposes, previous treatment, the patient's clinical history and response to the agent, and the discretion of the attending physician. Typically, the clinician will administer a peptide-phospholipid conjugate, until a dosage is reached that achieves the desired result. In some cases, sustained continuous release formulations of a peptide-phospholipid conjugate may be appropriate. Various formulations and devices for achieving sustained release are known in the art.

In one embodiment, dosages for peptide-phospholipid conjugates may be determined empirically in individuals who have been given one or more administration(s). Individuals are given incremental doses of peptide-phospholipid conjugates. To assess efficacy of peptide-phospholipid conjugates, markers of the disease symptoms can be monitored.

Administration of a peptide-phospholipid conjugate in accordance with the methods of the present invention can be continuous or intermittent, depending, for example, upon the recipient's physiological condition, whether the purpose of the administration is therapeutic or prophylactic, and other factors known to skilled practitioners. The administration of may be essentially continuous over a preselected period of time or may be in a series of spaced dosages, e.g., either before, during, or after the insurgence of atherosclerosis.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

In some embodiments, more than one peptide-phospholipid conjugate may be administered, for example in compositions that may contain at least one, at least two, at least three, at least four, at least five different peptide-phospholipid conjugates. A mixture of peptide-phospholipid conjugates may be particularly useful in treating a broader range of population of individuals.

EXAMPLES

Example 1

A number of peptide-phospholipid conjugates of POVPC, respectively numbered 3, 4, 5, 6, and 23-28 were synthesized and tested. Conjugates 3, 4 and 5 were found to be stable and characterized by affinity for macrophages and T-cells, but exhibited poor water solubility:

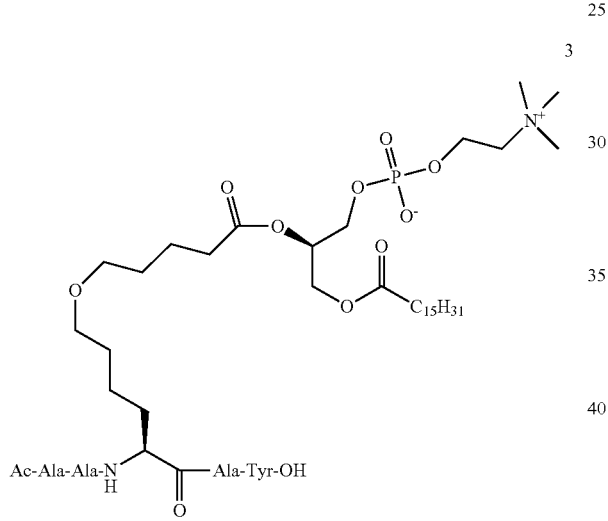

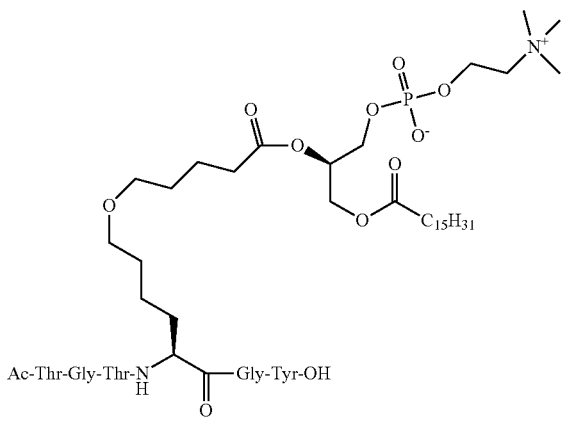

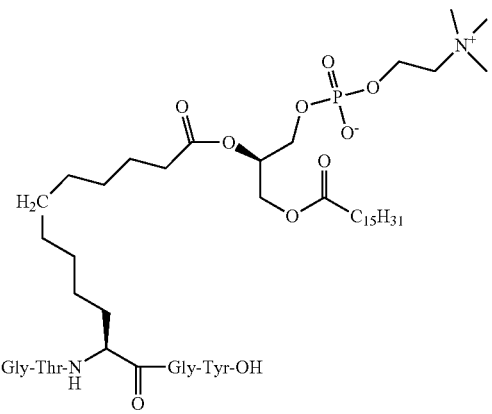

By contrast, peptide-phospholipid conjugates 6 and 23-38 were stable, showed affinity for macrophages and T-cells, but were also soluble in aqueous buffers:

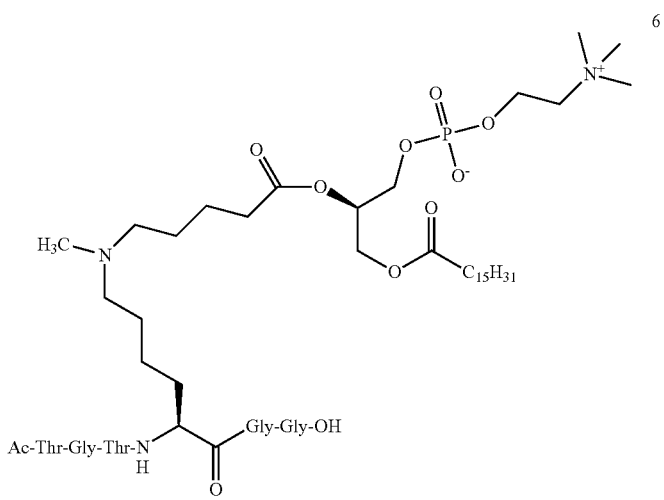

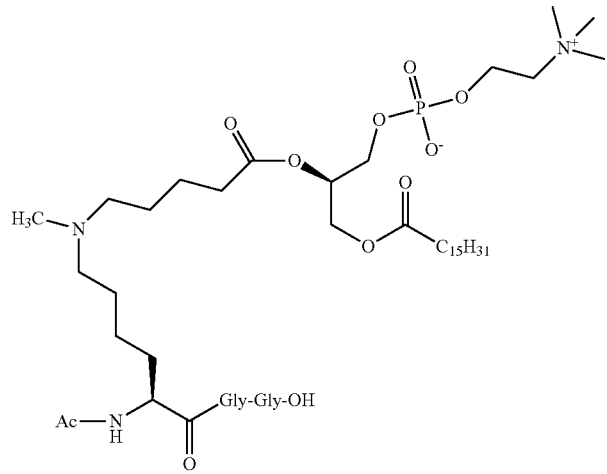
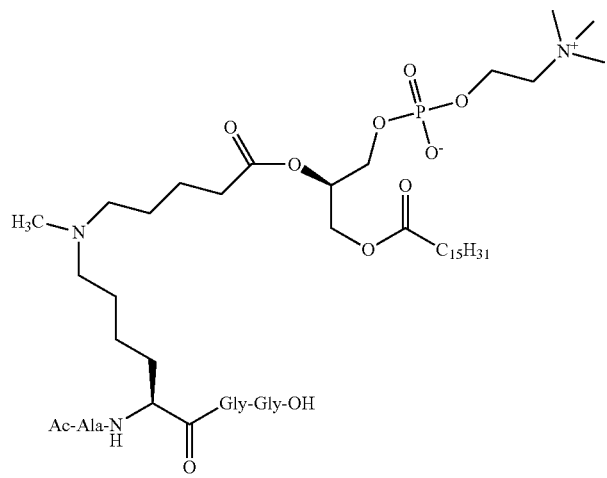
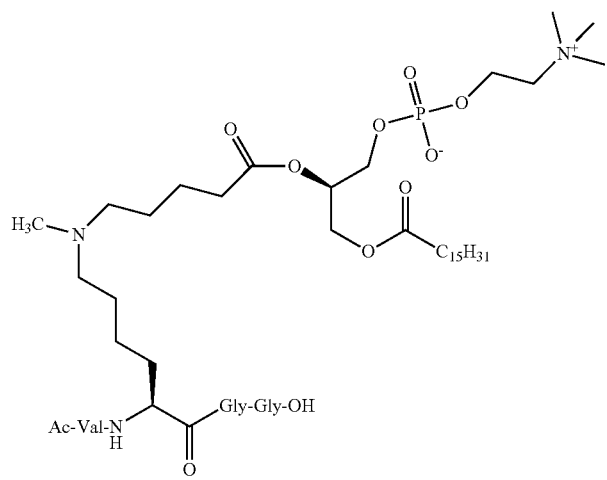

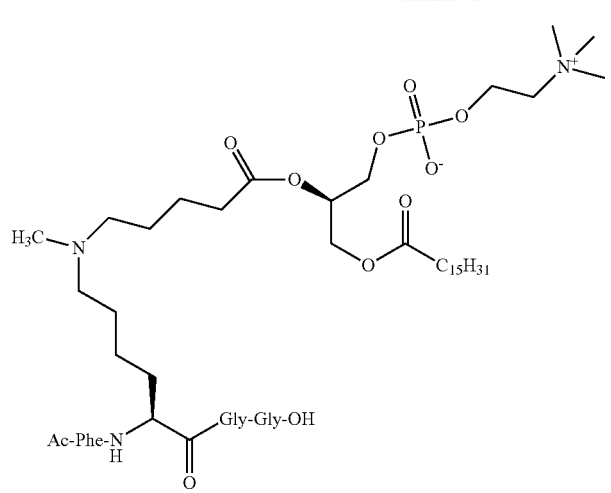

26

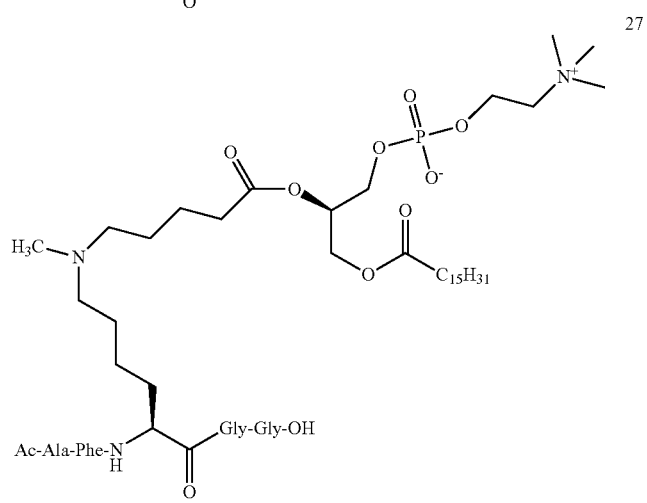

27

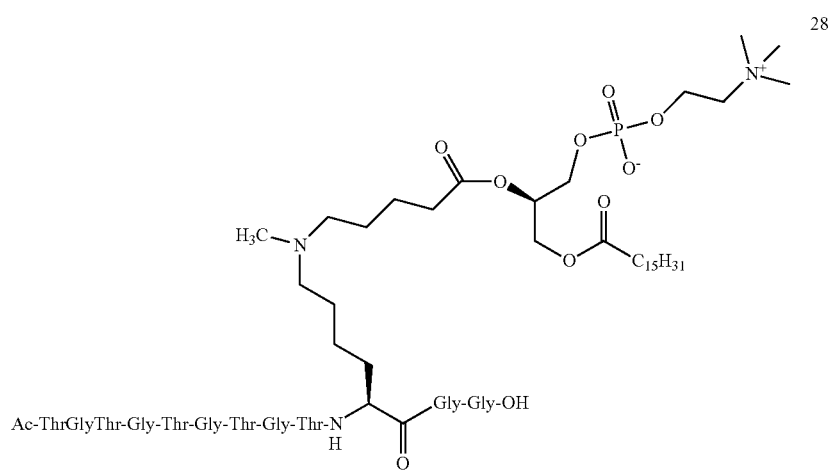

28

Without being bound to any particular theory, it is believed that the poor solubility of 3, 4, and 5 is due to their respective peptides featuring hydrophobic amino acids alanine and/or tyrosine and to their respective non-basic linking moieties where X is —O— or —CH$_2$—, whereas 6 and 23-28 include less lypophilic amino acids threonine and/or glycine and feature a basic linking moiety where X is a —N(CH$_3$)— group. It should also be noted that 6 and 23-28 demonstrate that activity is present irrespective of the fact that the respective peptides differ in size, thereby confirming the hypothesis that the composition of the peptide moiety appears not to matter, provided that it enhances the solubility of the conjugate in aqueous media.

Example 2

Synthesis of Compound 6

Figure 2:
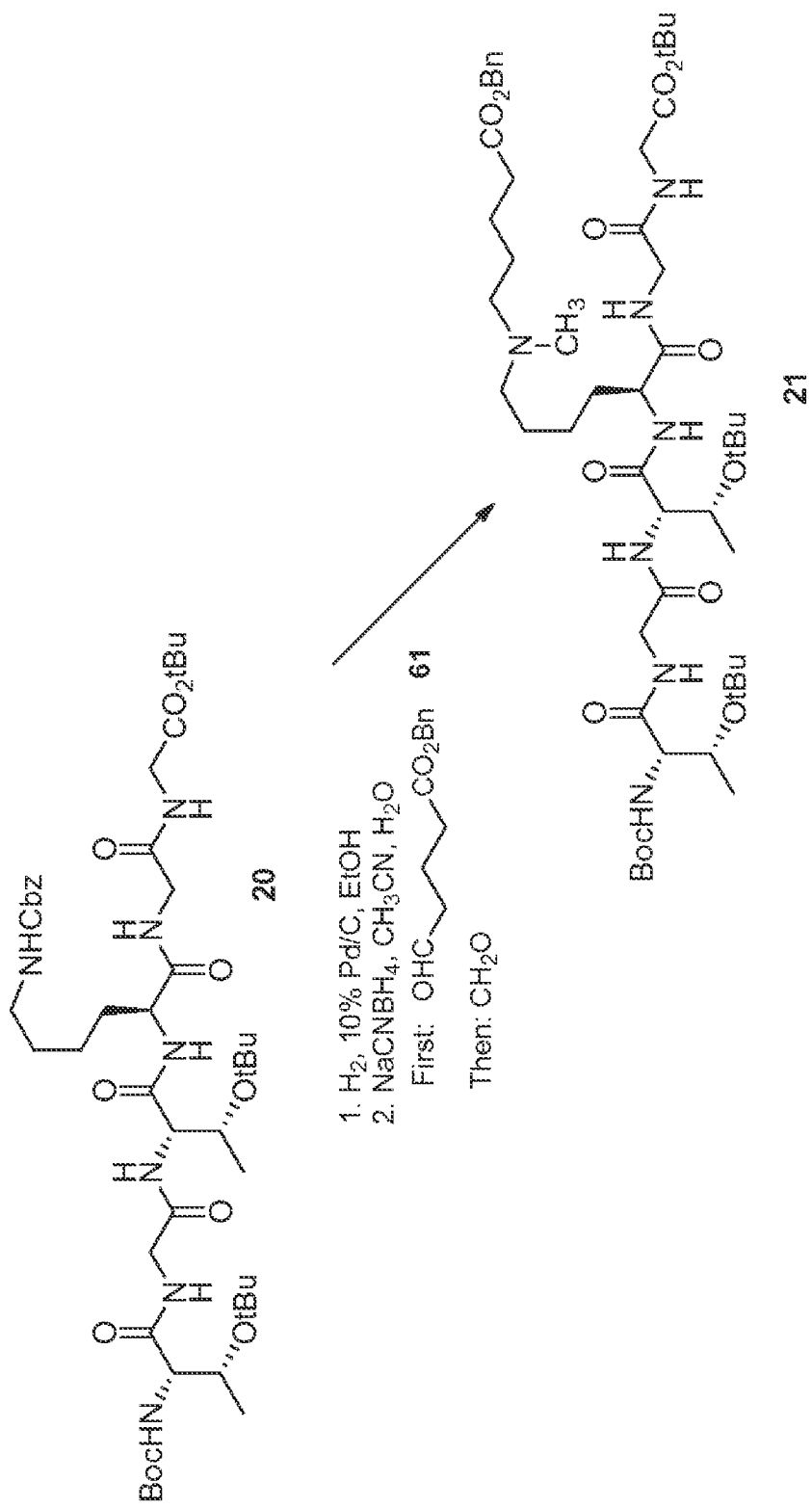
FIG. 2 illustrates a synthetic scheme for the synthesis of compound 6.
Figure 2:
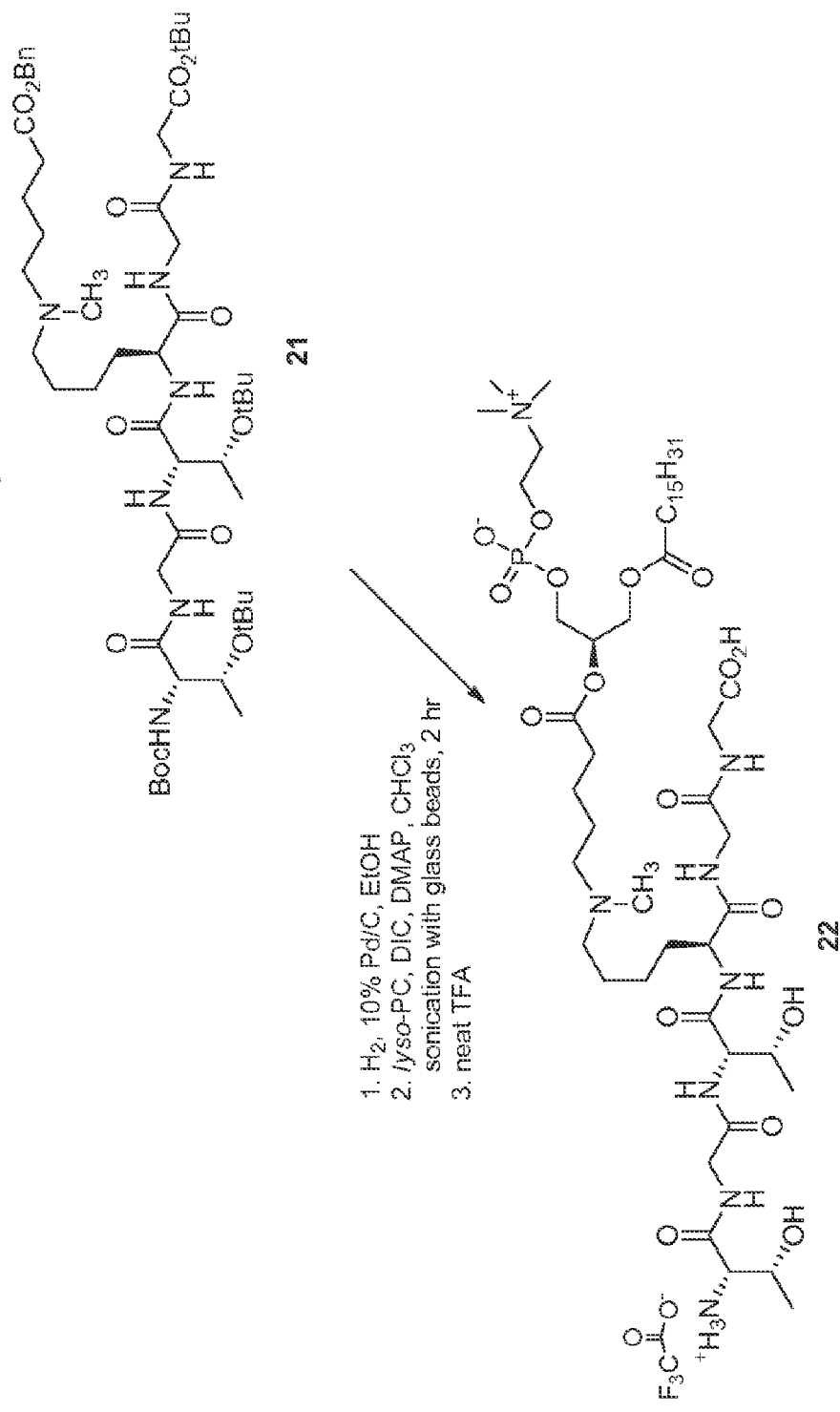
Figure 2:
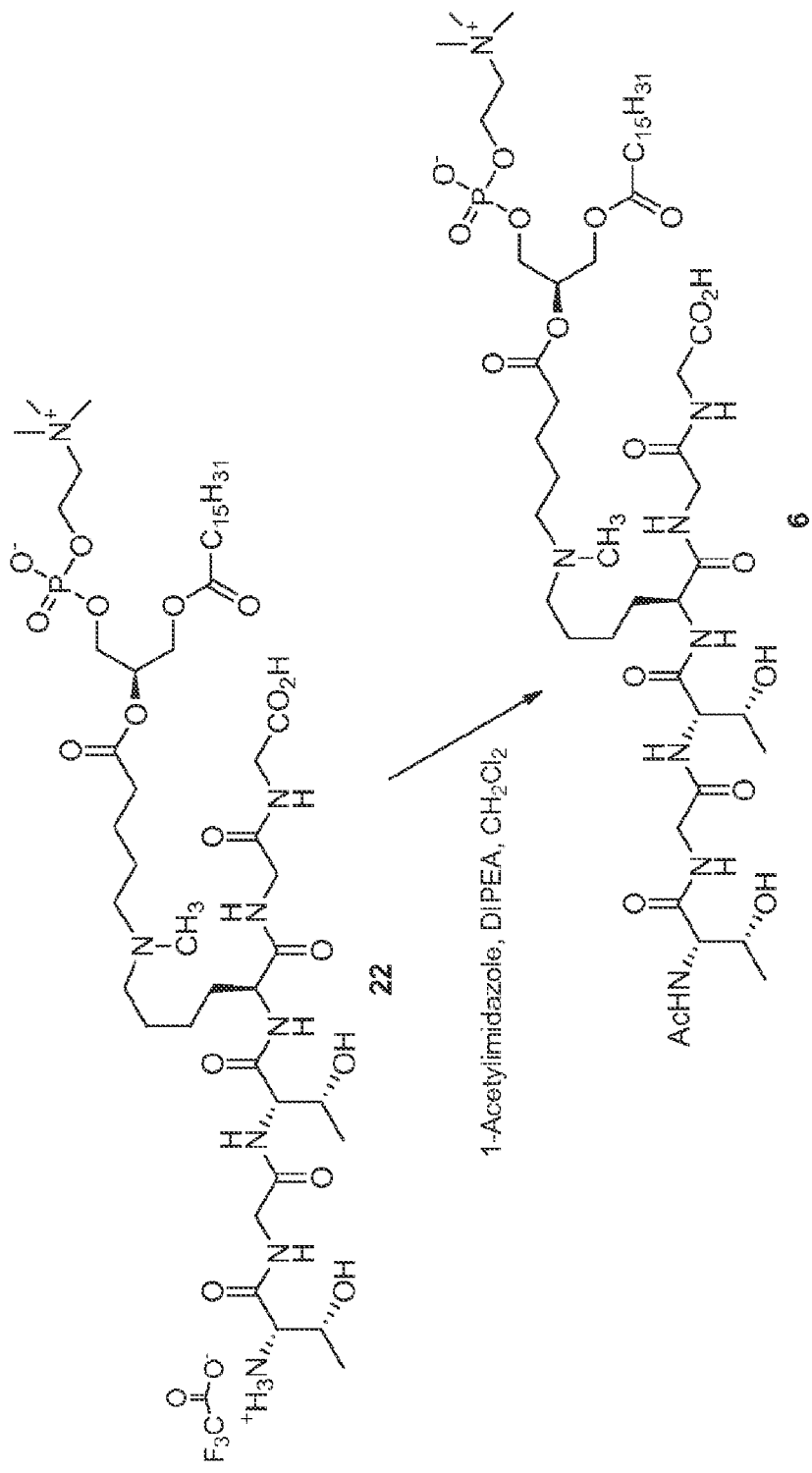

Conjugate 6 was prepared according to the synthetic scheme of FIG. 2. The appropriately protected hexapeptide (20) was prepared using a manual Fmoc solid phase peptide synthesis followed by esterification of the acid terminus. The ε-amine of the lysine unit of 20 was revealed by cleavage of the carbonyl benzyloxy (Cbz) protecting group and a double reductive alkylation was performed to generate the tertiary amino compound (21). This single pot double alkylation was conducted by first treating the amine with 1.3 equivalents of aldehyde 61 (NaCNBH$_3$, AcOH, CH$_3$CN, H$_2$O, 1 hr) giving predominately monoalkylation followed by the addition of excess 37% aqueous formaldehyde solution to provide the second alkylation and the tertiary amine. Using this technique, mixtures with about 80% of the appropriate mixed dialkylated amine could be generated with only minor amounts of the compounds with either two formaldehyde units or two units of 61 attached. After purification, the benzyl ester of 21 was removed by hydrogenation to give the acid group needed for coupling to lyso-PC. A survey of the literature uncovered a carbodiimide ester coupling technique using sonication[19] that greatly improved on the time of reaction and the yield of the coupling. The carboxylic acid compound was converted to the ester using lyso-PC (3 equivalents, hereinafter "eq"). diisopropylcarbodiimide (DIC) (2 eq), and 4-dimethylaminopyridine (DMAP) (2 eq) in chloroform in 2 hours with a yield of 68% using sonication in the presence of glass beads to increase the glass surface area. Couplings done using more traditional solution methodology took several days with yields of 20-30%. The product was globally deprotected (TFA, 0° C. 2 hr) to give 22 and the amino terminus of the peptide was acylated (1-acetylimidazole, DIPEA, CH$_2$Cl$_2$) to give final compound 6.

Example 3

Binding of 6 to Macrophages

Figure 3A:
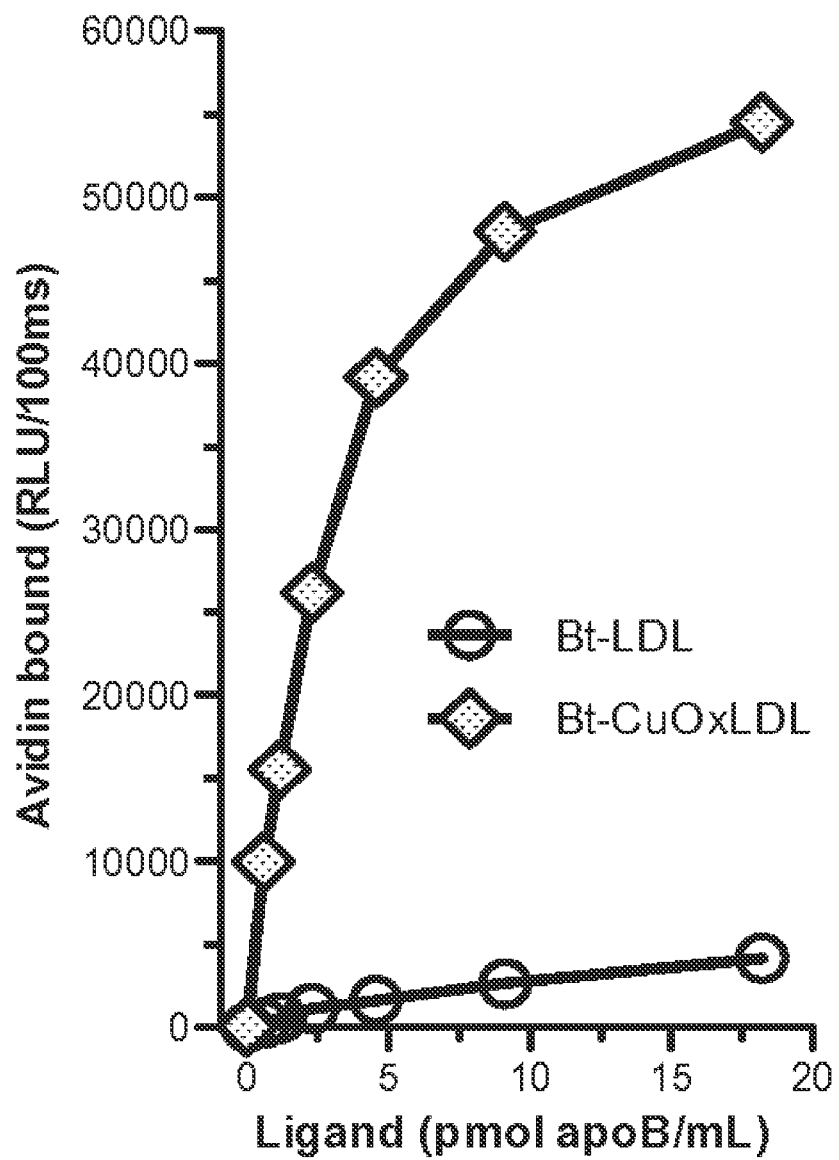
FIG. 3 illustrates the results of competitive binding experiments.
Figure 3B:
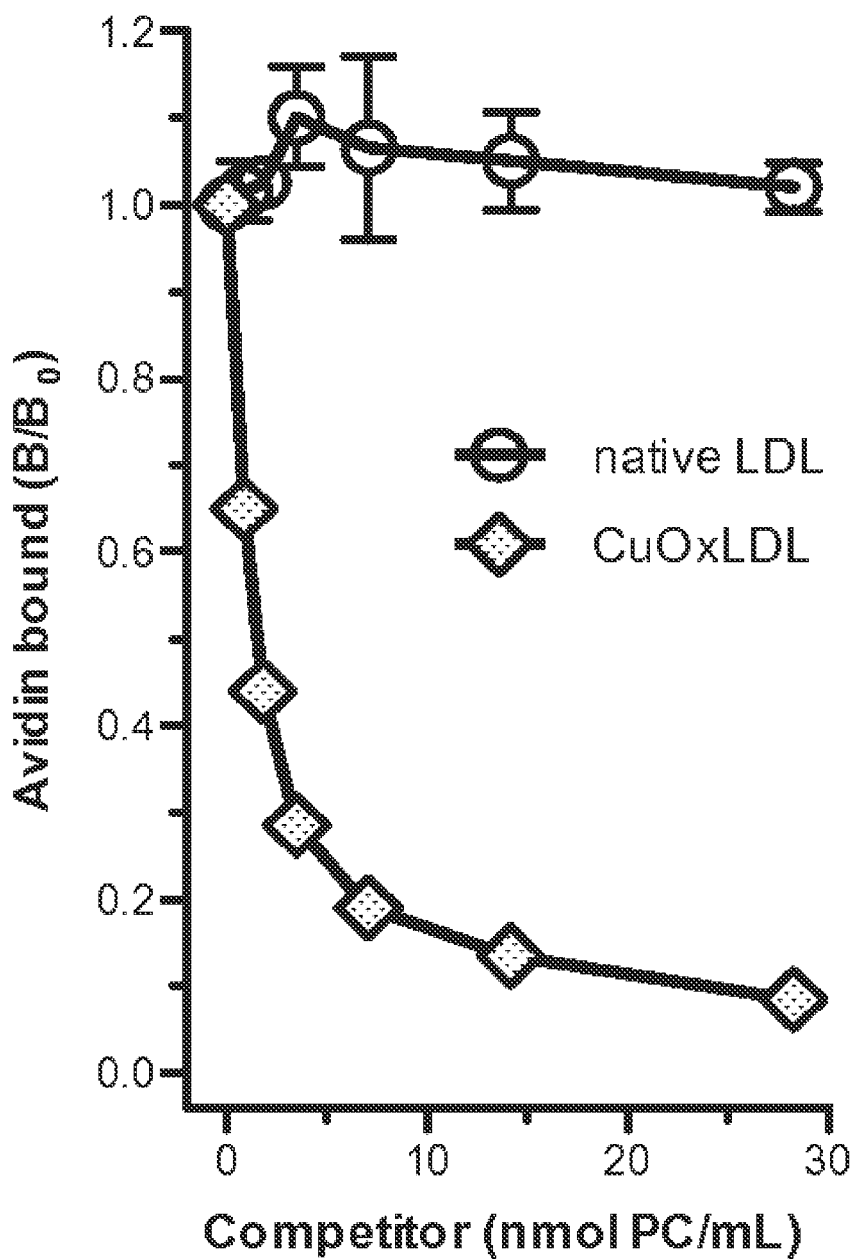
Figure 3C:
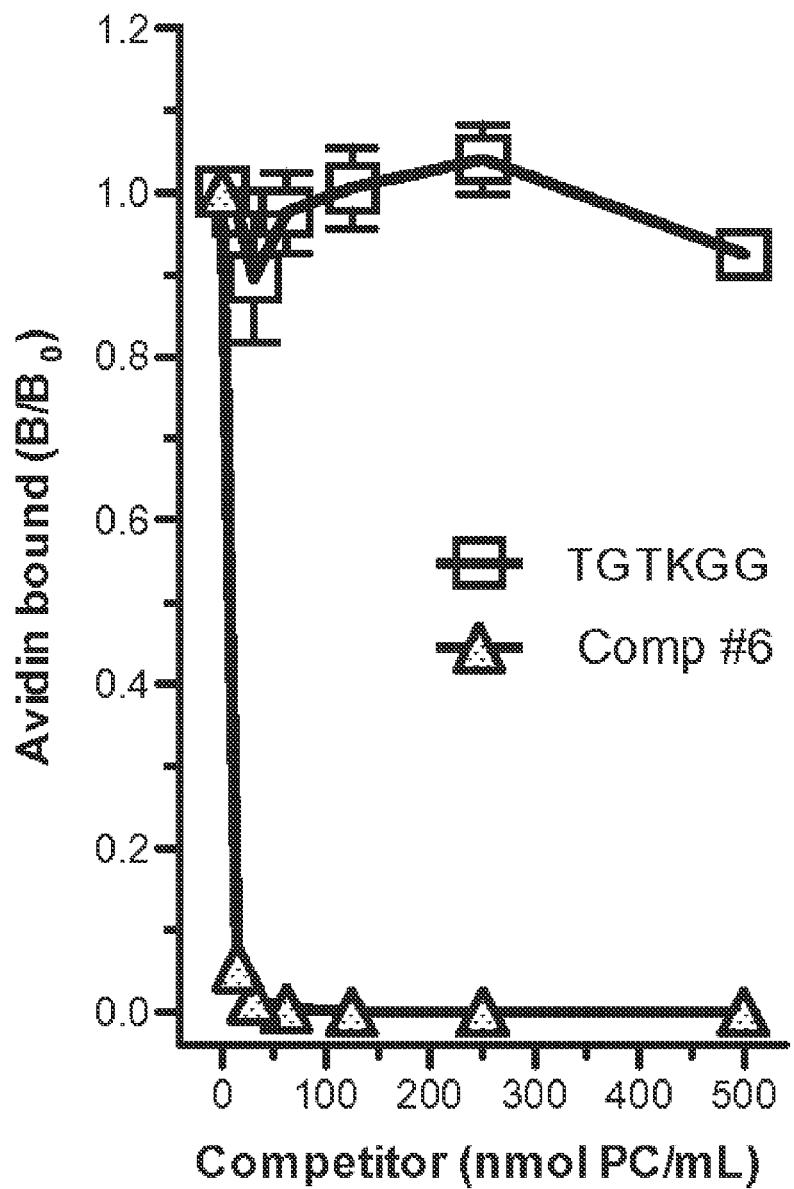

As illustrated in FIG. 3, compound 6 efficiently competed for binding of biotinylated copper-oxidized LDL (CuOxLDL) to J774 murine macrophages. With reference to FIG. 3A, an in vitro binding experiment showed that biotinylated CuOxLDL (diamonds) bound in a dose-dependent and saturable manner to J774 macrophages, whereas native LDL (circles) did not. Data are given as relative light units (RLU) per 100 ms (milliseconds). The plot is a representative experiment chosen from among at least four experiments. As shown in FIG. 3B, CuOxLDL (diamonds), but not native LDL (circles), competed for Bt-CuOxLDL (1.5 µg/mL) binding to J774 macrophages. Data are shown as mean±SD (Standard Deviation) of B/B$_0$ from 2 independent experiments with triplicate determination. As illustrated in FIG. 3C, compound 6 (triangles), but not control peptide TGTKGG (squares), competed for Bt-CuOxLDL (1.5 µg/mL) binding to J774 macrophages. Data are shown as mean±SD of B/B$_0$ from two independent experiments with triplicate determination. Data in FIG. 3B and FIG. 3C were produced in parallel experiments.

Compound 6 as well as the positive control, unlabelled CuOxLDL, competed at more than 99% and 90%, respectively, with biotinylated CuOxLDL binding to macrophages, whereas the control peptide TGTKGG and native LDL did not compete. The fixed concentration of biotinylated CuOxLDL (1.8 pmol apoB/mL, corresponding 1 µg apoB/mL or 0.14 nmol PC-epitopes/mL) was preincubated with compound 6, the control peptide TGTKGG, CuOxLDL, or native LDL, added at the concentrations indicated on the graphs, and then tested for binding as described in the experimental section. The highest CuOxLDL concentration tested was 200 µg/mL, which corresponds to approximately 28.3 nmoles of PC-epitopes/mL, as estimated from the previous observation that 1 mole of apoB-100 from CuOxLDL contains 78±15 moles of covalently attached phosphorus[10], which it is assumed are PC-epitopes only. The concentration of native LDL is plotted at equal protein concentration to CuOxLDL (and thus not as molar concentration of PC-epitopes). Each data point represents the mean and SD of 2 independent experiments of triplicate wells. This result implies a strong, specific binding with the CD36 macrophage receptor.

Example 4

Biological Test Data

Each of peptide-phospholipid conjugates 6 and 23-27 were tested as competitors in a CD36 macrophage receptor binding competition assay, where fixed concentrations of CuOxLDL were incubated with the serially diluted competitor and controls in PBS buffer. The IC$_{50}$ of each competitor is reported below in Table 1, confirming the affinity of the compounds of the invention for the CD36 macrophage receptor:

TABLE 1

| Compound No. | IC$_{50}$ (µM) |
|---|---|
| 6 | 60 |
| 23 | 38 |
| 24 | 131 |
| 25 | 55 |
| 26 | 47 |
| 27 | 47 |

Figure 4:
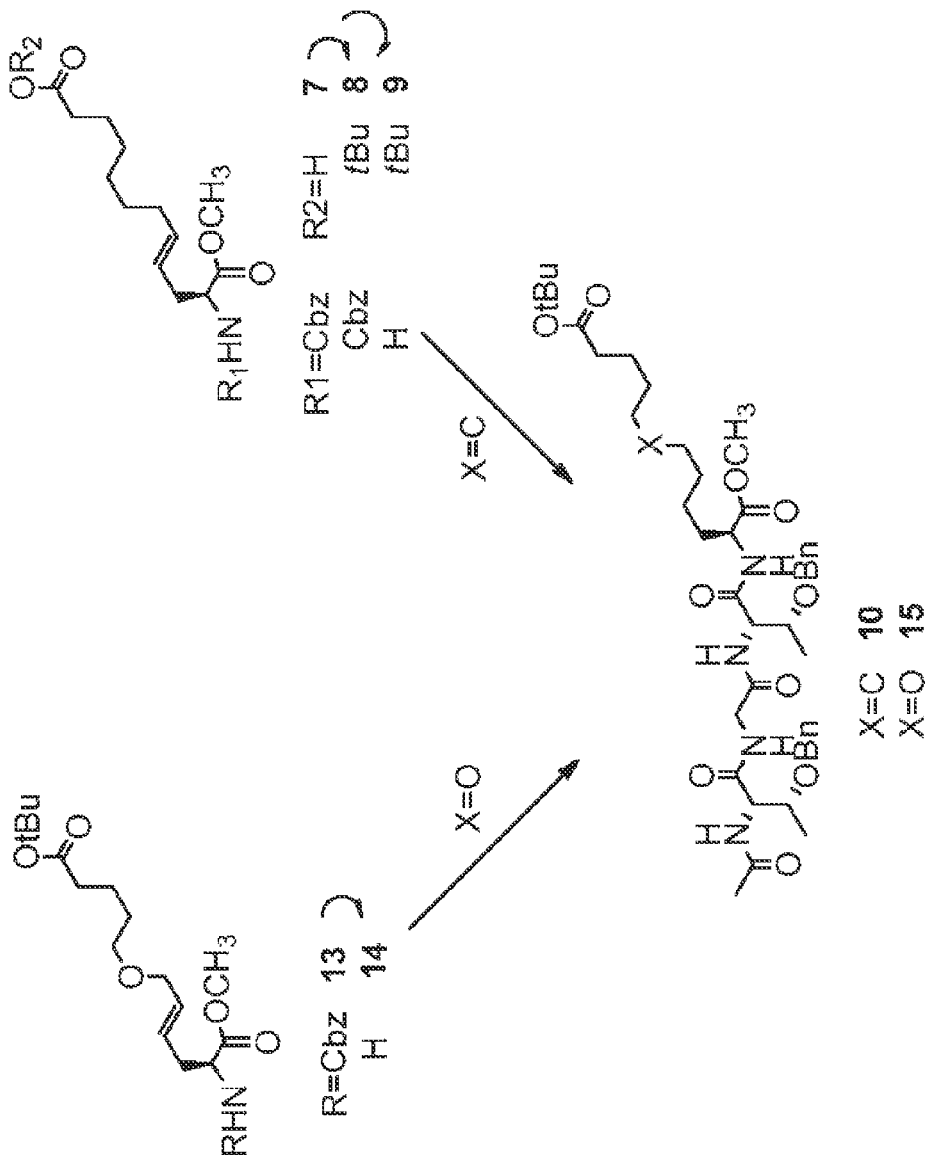
FIG. 4 illustrates a synthetic scheme for the synthesis of compounds 4 and 5.
Figure 4:
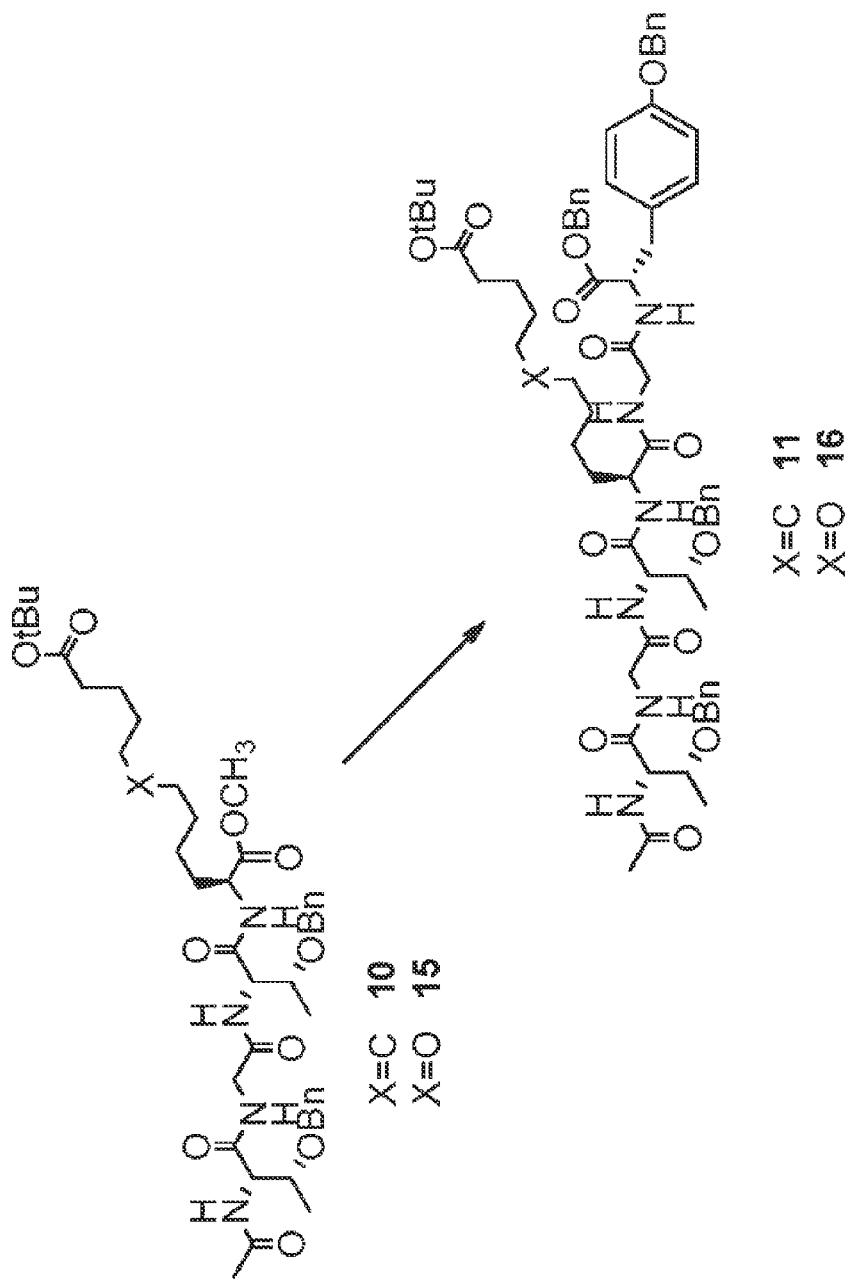
Figure 4:
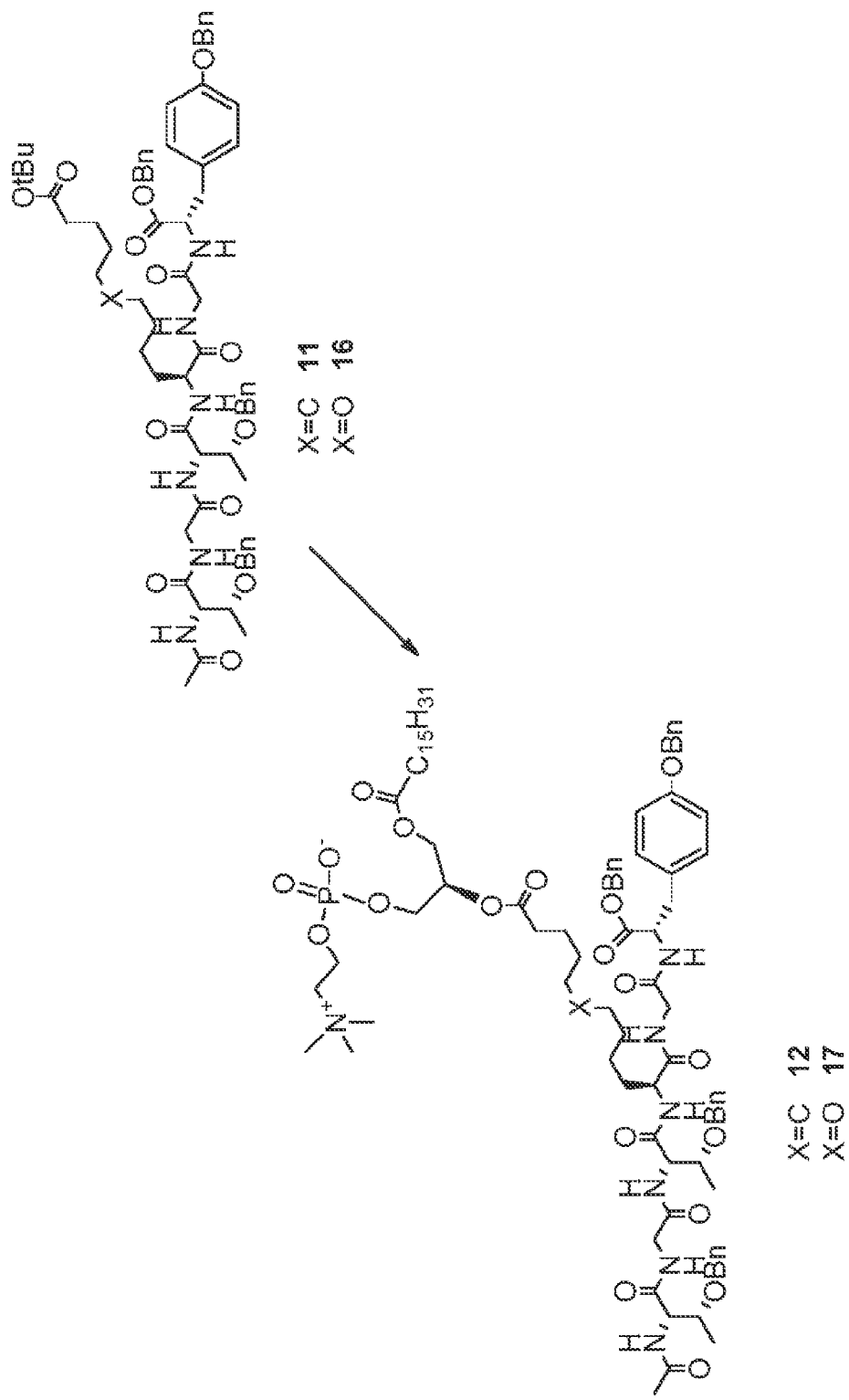
Figure 4:
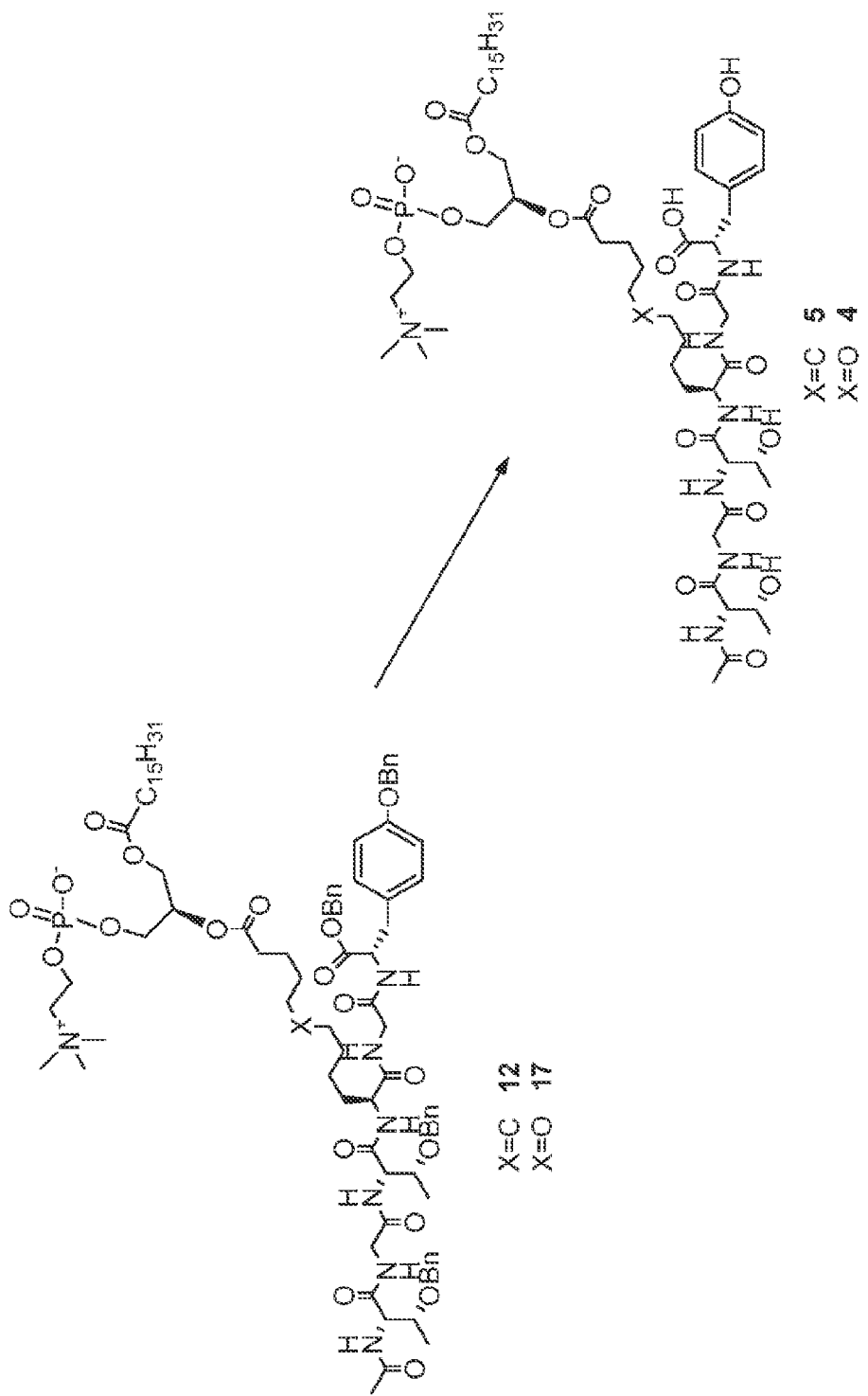

Experimental Section
Synthesis of Compounds 4 and 5
A synthesis of compounds 4 and 5 was performed according to the synthetic scheme illustrated in FIG. 4.

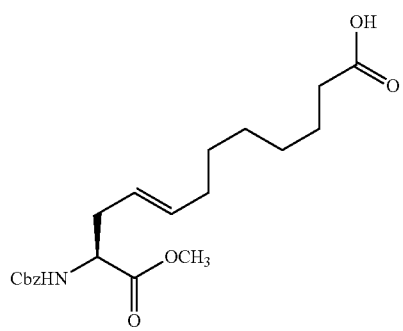

Synthesis of 7:
(8-t-Butoxy-8-oxooctyl)triphenylphosphonium bromide (4.32 g, 8.9 mmol, 1.2 eq) was suspended in 60 of toluene at 0° C. under argon. A solution of potassium hexamethyldisilazane (34.12 mL, 17.06 mmol, 2.3 eq) was added dropwise giving a red solution which was stirred at 0° C. for 0.5 hr and then at room temperature for 1 hr. The reaction was cooled to −78° C. and (S)-methyl 2-(bis(tert-butoxycarbonyl)amino)-4-oxobutanoate (2.46 g, 7.42 mmol, 1 eg) in toluene was added dropwise. After 4 hr the reaction was quenched with 10% HCl solution and extracted with ethyl acetate. The organic layer was dried over anhydrous sodium sulfate and reduced in vacuo to give the crude product oil. Purification over a Biotage silica column gave 2.14 g (62%) of pure (S,E)-12-t-butyl 1-methyl 2-(bis(t-butoxycarbonyl)amino)dodec-4-enedioate. A portion of this compound (1.4 g, 3.06 mmol, 1 eq) was dissolved in 4M HCl solution in 1,4-dioxane (75 mL, 306 mmol, 100 eq) and stirred at room temperature for 20 min. The solvent was evaporated in vacuo and the residue was dissolved in tetrahydrofuran (20 mL). A solution of sodium carbonate (1.95 g, 18.36 mmol, 6 eq) in water (20 mL) was added and the reaction was cooled to 0° C. Benzyl 2,5-dioxopyrrolidin-1-yl carbonate (915 mg, 3.67 mmol, 1.2 eq) was added and the cooling bath removed and stirring continued for 18 hr. The reaction mixture was acidified with a dilute HCl solution and extracted with ethyl acetate. The organic extract was dried and reduced in vacuo to give a crude oil which was purified by flash chromatography to give 7 (970 mg, 81% yield) as a colorless oil.

Accurate EI MS: Found 391.1992. Calculated 391.1989 for $C_{21}H_{29}NO_6$ (M+).

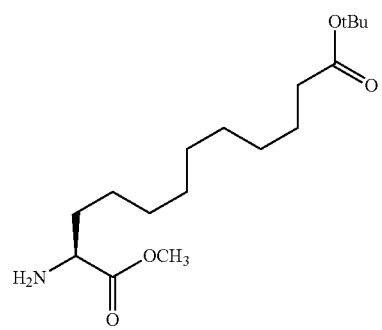

9

Synthesis of 9:

Compound 8 (316 mg, 0.71 mmol) was dissolved in methanol (7 mL) and this solution was added to 5% palladium on carbon (63.2 mg). This slurry was put under a balloon of hydrogen gas for 2 hr. The solution was filtered through celite which was washed with methanol. The combined washes were evaporated and the residual oil was dried in vacuo to give 9 (211 mg) as a yellow oil.

Accurate EI MS: Found 316.2478. Calculated 316.2482 for $C_{17}H_{34}NO_4$ (M+H+)

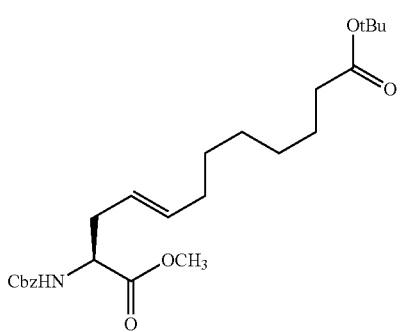

8

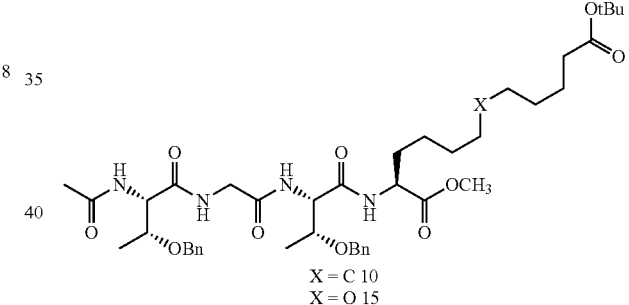

X = C 10
X = O 15

Synthesis of 10 and 15:

(2S,3R)-Methyl 2-(2-((2S,3R)-2-acetamido-3-(benzyloxy)butanamido)acetamido)-3-(benzyloxy)butanoate (1.24 g, 2.42 mmol, 1.3 eq) was hydrolyzed with lithium hydroxide monohydrate (132 mg, 3.15 mmol) in a mixture of 20 mL of tetrahydrofuran and 5 mL of water to give the free acid. This was mixed with 9 (588 mg, 1.86 mmol, 1 eq), EDC (464 mg, 2.42 mmol, 1.3 eq), HOAt (329 mg, 2.42 mmol, 1.3 eq) and sodium bicarbonate (203 mg, 2.42 mmol, 1.3 eq) in dimethylformamide (25 mL) and dichloromethane (25 mL). The reaction mixture was stirred at room temperature for 18 hr. The solvent was removed in vacuo and the crude product was purified by flash chromatography to give 10 (1.33 g, 90% yield) as a white foam.

Accurate FAB MS: Found 797.4686. Calculated 797.4695 for $C_{43}H_{65}N_4O_{10}$ (M+H+).

In a similar manner, 14 (752 mg, 2.37 mmol) afforded 15 (1.68 g, 89% yield) as a white solid.

Accurate EI MS: Found 798.4382. Calculated 798.4410 for $C_{42}H_{62}N_4O_{11}$ (M+)

Synthesis of 8:

Compound 7 (497 mg, 1.27 mmol) was dissolved in a mixture of dichloromethane (6 mL) and cyclohexane (12 mL). t-Butyl trichloroacetamide (832 mg, 3.81 mmol, 3 eq) and 4 A molecular sieve (500 mg) were added, the solution cooled to 0° C., and boron trifluoroetherate (25 mL) was added. The cooling bath was removed and the reaction was stirred for 17 hr. The reaction was quenched with solid sodium carbonate, the solids removed by filtration, and the solvent removed in vacuo. Purification by flash chromatography afforded 8 (443 mg, 78% yield) as a colorless oil.

ESI MS: Found 470.17 for $C_{25}H_{37}NO_6$ (M+Na+)

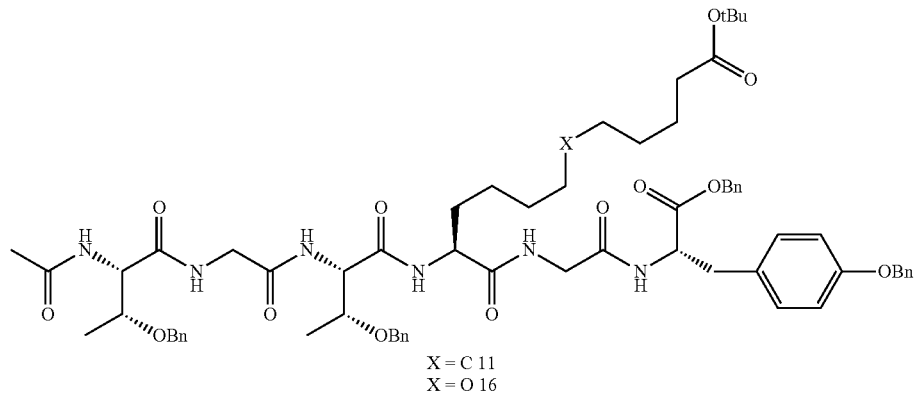

X = C 11
X = O 16

Synthesis of 11 and 16:

Compound 10 (429 mg, 0.54 mmol, 1 eq) was hydrolyzed with lithium hydroxide monohydrate (29 mg, 0.70 mmol) in a mixture of 5 mL of tetrahydrofuran and 1 mL of water to give the free acid. This was mixed with (S)-benzyl 2-(2-aminoacetamido)-3-(4-(benzyloxy)phenyl)propanoate (344 mg, 0.65 mmol, 1.2 eq), EDC (134 mg, 0.70 mmol, 1.3 eq), HOAt (95 mg, 0.70 mmol, 1.3 eq) and sodium bicarbonate (59 mg, 0.70 mmol, 1.3 eq) in dimethylformamide (5 mL) and dichloromethane (5 mL). The reaction mixture was stirred at room temperature for 18 hr. The solvent was removed in vacuo and the crude product was purified by flash chromatography to give 11 (517 mg, 81% yield) as a white solid.

Accurate ESI MS: Found 1183.6307. Calculated 1183.6325 for $C_{67}H_{87}N_6O_{13}$ (M+H$^+$).

In a similar manner, 15 (272 mg, 0.34 mmol) was converted to 16 (318 mg, 79% yield).

Accurate ESI MS: Found 1185.6094. Calculated 1185.6118 for $C_{66}H_{85}N_6O_{14}$ (M+H$^+$).

Synthesis of 12 and 17:

Compound 11 (251 mg, 0.212 mmol) was dissolved in 3 mL of 20% trifluoroacetic acid in dichloromethane and stirred at room temperature for 1 hr. The solvent was evaporated and the crude oil was purified over a flash column to remove the t-butyl ester and give the free acid form of 11 (217 mg, 86% yield) as a white solid. This free acid (60.9 mg, 0.054 mmol, 1 eq), was mixed with lyso-PC (32.1 mg, 0.065 mmol, 1.2 eq), dicyclohexylcarbodiimide (16.7 mg, 0.081 mmg, 1.5 eq) and 4-dimethylaminopyridine (7.9 mg, 0.065 mmol, 1.2 eq) in dimethylformamide (0.5 mL) and chloroform (0.5 mL). The reaction mixture was stirred at room temperature for 48 hr. The solvent was removed in vacuo and the crude product was purified using a reverse phase $C_{18}HS$ Biotage column (60-100% methanol/water eluant). Reduction of the pure fraction in vacuo afforded 12 (49 mg, 56% yield) as a white solid.

Accurate ESI MS: Found 1604.8915. Calculated 1604.8918 for $C_{87}H_{127}O_{19}P$ (M+H$^+$).

In a similar manner, 16 (317 mg, 0.27 mmol) (80 mg, 0.071 mmol) was converted to 17 (49 mg, 43% yield).

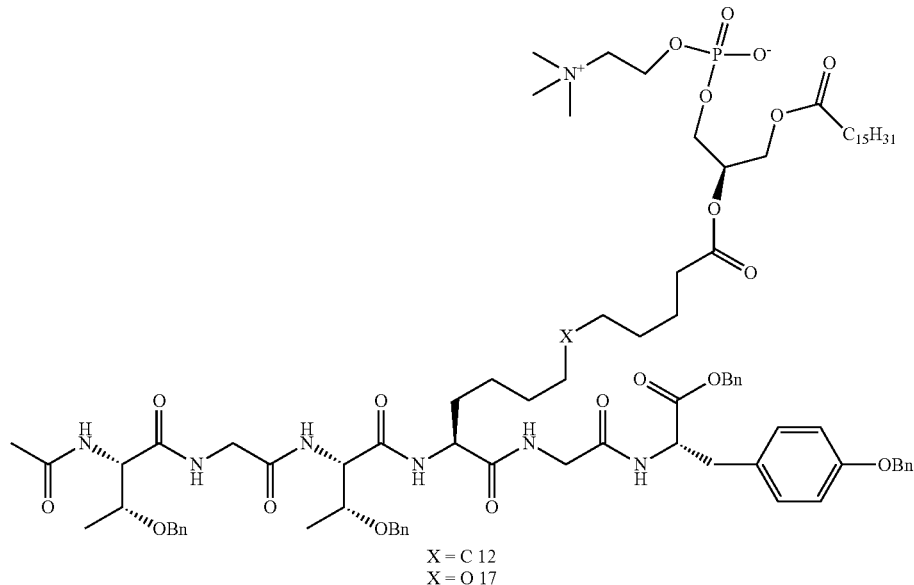

X = C 12
X = O 17

Accurate ESI MS: Found 1606.8667. Calculated 1606.8711 for $C_{86}H_{125}O_{20}P$ (M+H$^+$).

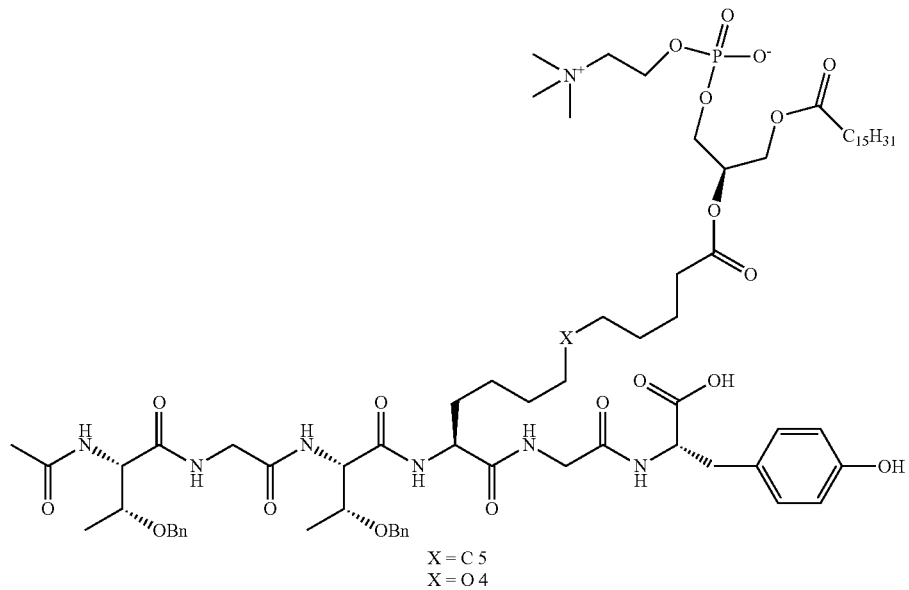

X = C 5
X = O 4

Synthesis of 5 and 4:

Compound 12 (97 mg, 0.060 mmol) was dissolved in methanol (2 mL) and added to 10% Pd/C (38 mg). The slurry was placed under 50 psi of hydrogen gas in a Parr shaker for 12 hr. The catalyst was removed by filtration through celite and the solvent was removed in vacuo. The crude product was purified by reverse phase HPLC to give 5 (54.9 mg, 73% yield) as a white solid.

Accurate ESI MS: Found 1244.7009. Calculated 1244.7041 for $C_{59}H_{103}N_7O_{19}P$ (M+H$^+$).

In a similar manner, 17 (102 mg, 0.063 mmol) was converted to 4 (62.5 mg, 79% yield) as a white solid.

Accurate ESI MS: Found 1246.6784. Calculated 1246.6833 for $C_{58}H_{101}N_7O_{20}P$ (M+H$^+$).

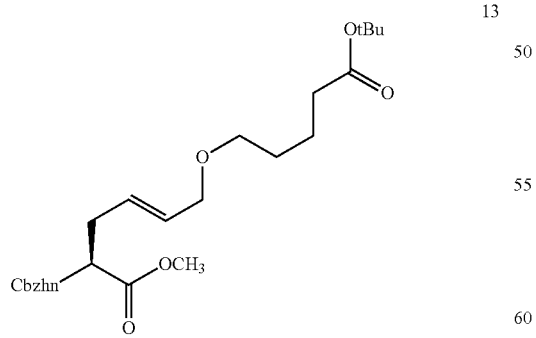

13

Synthesis of 13:

tert-Butyl 5-(allyloxy)pentanoate (1.0 g, 4.67 mmol, 1 eq) and (S)-methyl 2-(benzyloxycarbonylamino)pent-4-enoate (2.46 g, 9.34 mmol, 2 eq) were dissolved in dry dichloromethane (50 mL) in an oven-dried round bottom flask. The 2$^{nd}$ generation Grubb's catalyst (146 mg, 0.234 mmol, 0.05 eg) was added and the reaction was stirred for 4 hr at room temperature. The solvent was removed in vacuo and the crude product was purified by flash chromatography (10-33% ethyl acetate/hexane). The pure fraction was reduced in vacuo to give 13 (646 mg, 31% yield) as an oil.

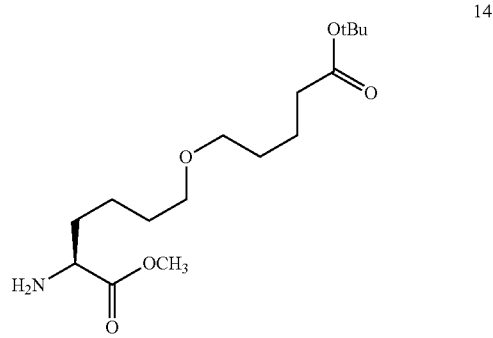 [SMILES: COC(=O)[C@@H](N)CCCCOCCCCC(=O)OC(C)(C)C]

14

Synthesis of 14:

Compound 13 (640 mg, 1.42 mmol) was dissolved in methanol (7 mL) and added to 10% Pd/C (128 mg). The slurry was placed under a balloon of hydrogen for 75 min. The catalyst was removed by filtration through celite and the solid was washed with 150 mL of methanol. The combined washes were reduced in vacuo to give 14 which was used directly in the next reaction.

Figure 5:
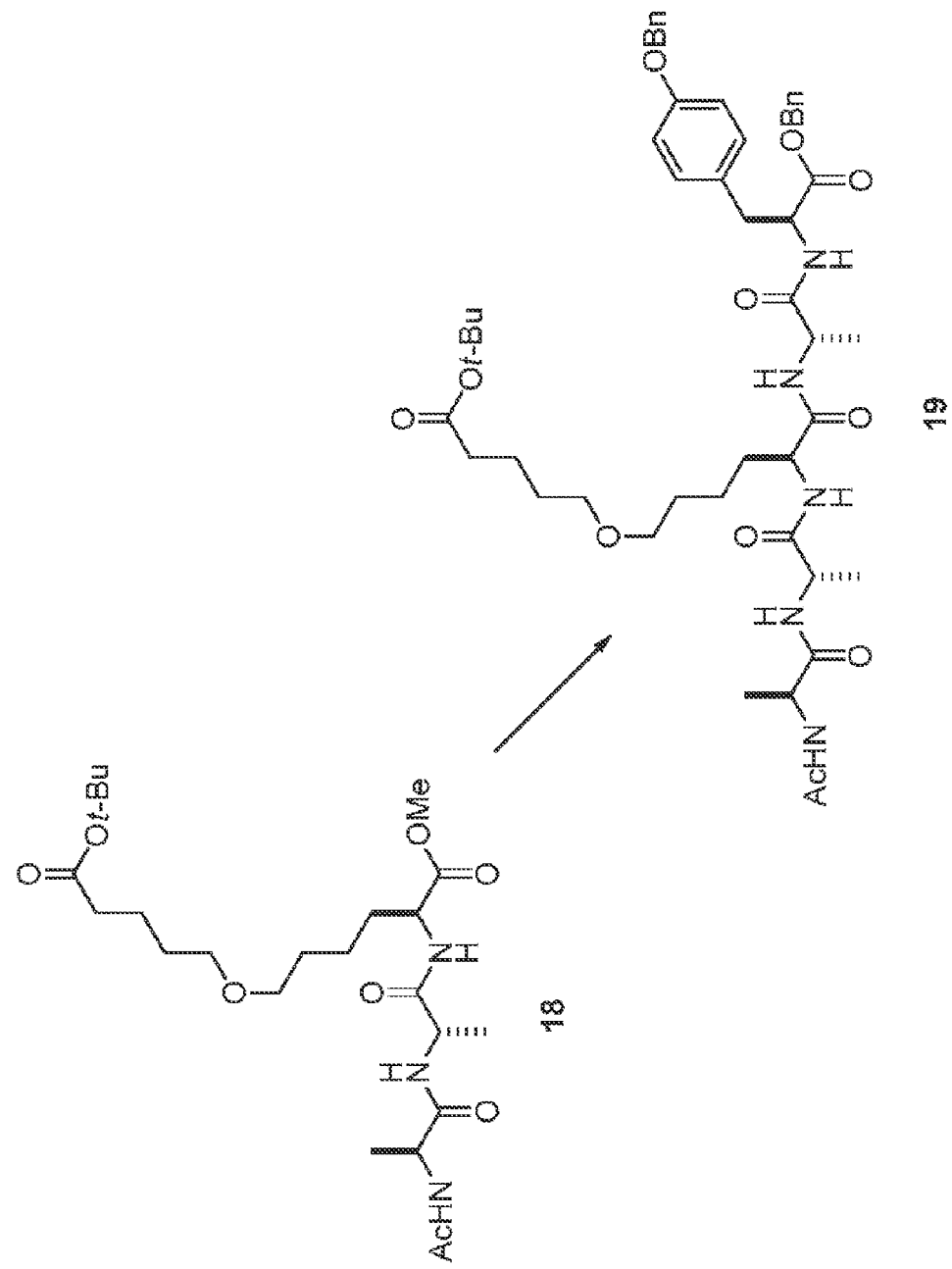
FIG. 5 illustrates a synthetic scheme for the synthesis of compound 3.
Figure 5:
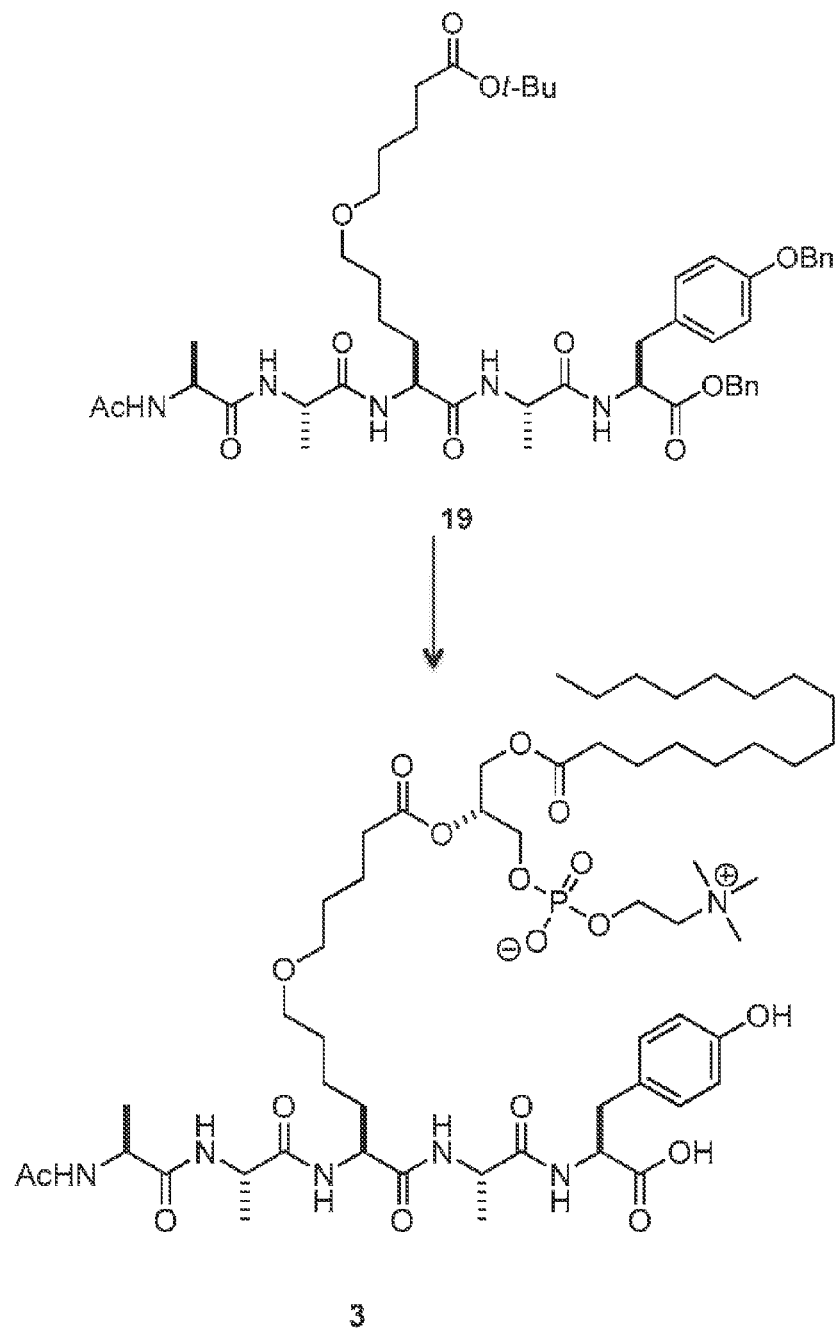

The synthesis of compound 3 was carried out according to the synthetic scheme illustrated in FIG. 5.

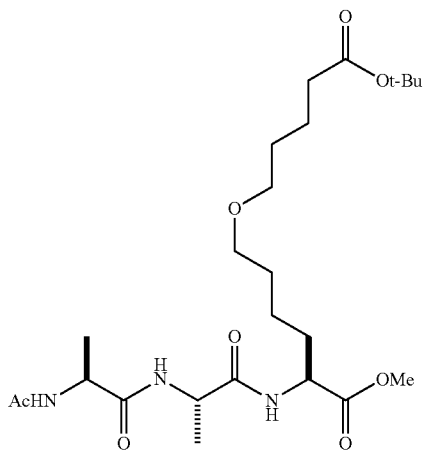

18

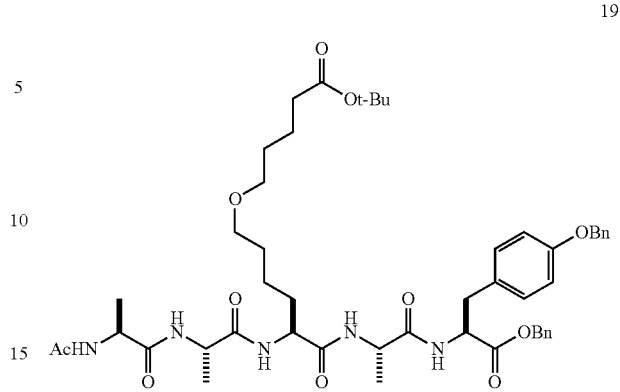

19

Synthesis of 18:

A solution of t-butyl 5-(allyloxy)pentanoate (420 mg, 1.96 mmol) and (S)-methyl 2-(benzyloxycarbonylamino) pent-4-enoate (3.1 g, 11.8 mmol) in anhydrous $CH_2Cl_2$ (20 mL) was treated with Hoveyda-Grubbs catalyst second generation (61 mg, 0.098 mmol). The resulting mixture was stirred under an atmosphere of $N_2$ for 1.5 hr and then concentrated. The residue was chromatographed on silica gel (36% EtOAc/hexanes) to yield 290 mg of impure disubstituted alkene as a pale yellow oil and white particles.

A mixture of disubstituted alkene and 10% palladium on carbon (58 mg) in MeOH (3.2 mL) was stirred under an atmosphere of $H_2$ for 10 h. The reaction mixture was filtered through a pad of Celite® 545 and a glass frit (M porosity), the pad and frit were rinsed with MeOH, and the filtrate was concentrated. Filtration and concentration was repeated to yield crude amine as an oil, a black powder, and a white particle.

A suspension of amine, N-acetylalanylalanine (156 mg, 0.774 mmol), HOAt (114 mg, 0.838 mmol), and $NaHCO_3$ (70 mg, 0.838 mmol) in anhydrous DMF (1.6 mL) and anhydrous $CH_2Cl_2$ (1.6 mL) under an atmosphere of $N_2$ was cooled to 0° C. and treated with EDC (161 mg, 0.838 mmol), and the resulting mixture was stirred for 3 hr. The reaction was quenched with water and extracted 3 times with EtOAc. The combined organic layers were washed successively with 1 M HCl, sat. eq. $NaHCO_3$, and sat. eq. NaCl, dried over $Na_2SO_4$, filtered, and concentrated. The residue was chromatographed on silica gel (10% MeOH/$CHCl_3$) to yield 253 mg of 18 as a white film; $[\alpha]_D^{26}$ –27° (c 1.0, $CHCl_3$); $^1H$ NMR (400 MHz, DMSO-$d_5$) δ 1.16 (d, J=7.2 Hz, 3H), 1.20 (d, J=7.2 Hz, 3H), 1.26-1.36 (m, 2H), 1.39 (s, 9H), 1.41-1.54 (m, 6H), 1.55-1.74 (m, 2H), 1.82 (s, 3H), 2.18 (t, J=7.0 Hz, 2H), 3.28-3.34 (m, 4H, obscured by water), 3.60 (s, 3H), 4.16-4.33 (m, 3H), 7.95 (d, J=7.6 Hz, 1H), 8.02 (d, J=7.2 Hz, 1H), 8.10 (d, J=7.6 Hz, 1H); $^{13}C$ NMR (100 MHz, DMSO-$d_5$) δ 18.0, 21.4, 22.0, 22.4, 27.7, 28.4, 28.6, 30.6, 34.4, 47.6, 48.0, 51.7, 51.8, 69.4, 69.6, 79.3, 169.0, 171.9, 172.1, 172.2, 172.3; HRMS (ESI) $C_{24}H_{43}N_3O_8Na$ (M+Na) calculated 524.2948. found 524.2953.

Synthesis of 19:

A solution of 18 (200 mg, 405 μmol) in THF (4 mL) was treated with a 1 M solution of LiOH in water (450 μL, 445 μmol), and the resulting mixture was stirred for 4 h. The reaction was concentrated to a mostly aqueous mixture, which was freeze-dried to yield crude lithium carboxylate.

A suspension of this lithium carboxylate, (S)-benzyl 2-((S)-2-aminopropanamido)-3-(4-(benzyloxy)phenyl)propanoate trifluoroacetic acid salt (290 mg, 526 μmol), HOAt (72 mg, 526 μmol), and $NaHCO_3$ (68 mg, 809 μmol) in DMF (4.5 mL) and $CH_2Cl_2$ (1.4 mL) was cooled to 0° C. and treated with EDC (100 mg, 526 μmol). The reaction was stirred for 3 h. At some point during this time, the reaction was allowed to warm to room temperature. After this time the reaction was treated with additional EDC (20 mg, 121 μmol) and stirred for another 4 hr. The reaction was concentrated, the residue was partitioned between EtOAc and water, and the aqueous phase was extracted 4 times with EtOAc. The combined organic layers were washed successively with 1 M HCl, water saturated with $NaHCO_3$, and water saturated with NaCl, and concentrated. The residue was chromatographed on silica gel (2%→20% MeOH/$CHCl_3$ [smooth gradient]) with a Biotage SP1 purification system to yield 240 mg of 19 as a white solid; 1H NMR (400 MHz, DMSO-$d_6$) δ 1.14 (d, J=7.2 Hz, 3H), 1.17 (d, J=7.2 Hz, 3H), 1.19 (d, J=7.2 Hz, 3H), 1.21-1.31 (m, 2H). 1.38 (s, 9H). 1.39-1.53 (m, 7H), 1.55-1.66 (m, 1H), 1.82 (s, 3H), 2.16 (t, J=6.8 Hz, 2H), 2.86-2.98 (m, 2H), 3.24-3.31 (m, 4H), 4.15-4.32 (m, 4H), 4.43 (q, J=7.3 Hz, 1H), 5.04 (s, 2H), 5.05 (s, 2H), 6.88 (d, J=8.4 Hz, 2H), 7.10 (d, J=8.4 Hz, 2H), 7.22-7.26 (m, 2H), 7.29-7.46 (m, 8H), 7.76 (d, J=8.0 Hz, 1H), 7.91 (d, J=7.6 Hz, 1H), 8.04 (d, J=7.2 Hz, 1H), 8.06 (d, J=7.2 Hz, 1H), 8.28 (d, J=7.2 Hz, 1H); $^{13}C$ NMR (100 MHz, DMSO-$d_6$) δ 17.8, 17.9, 18.1, 21.4, 21.8, 22.3, 27.6, 28.4, 28.8, 31.7, 34.4, 35.7, 47.6, 48.0, 48.1, 52.1, 53.8, 65.8, 69.0, 69.4, 69.8, 79.2, 114.4, 127.5, 127.6, 127.7, 127.9, 128.2, 128.3, 128.8, 130.0, 135.6, 137.0, 157.0, 169.0, 170.8, 171.0, 171.9, 172.0, 172.1, 172.1; IR (KBr pellet) 3282, 2932, 1730, 1629, 1513, 1243, 1154 $cm^{-1}$; HRMS (ESI) $C_{49}H_{67}N_5O_{11}Na$ (M+Na+) calculated 924.4729. found 924.4735.

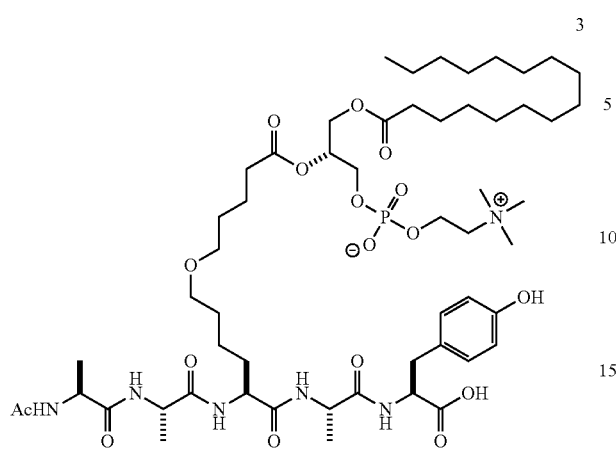

Compound 19 (230 mg, 252 µmol) in CH$_2$Cl$_2$ (2 mL) was treated with trifluoroacetic acid (0.5 mL), and the resulting solution was stirred for 3 hr. The reaction mixture was diluted with heptane (2 mL) and concentrated. Addition of heptane (2 mL) and concentration was repeated twice. The residue was chromatographed on silica gel (15% MeOH/CHCl$_3$) to yield 210 mg of carboxylic acid as an off-white solid.

A suspension of the carboxylic acid (66 mg, 78.0 µmol), 1-palmitoy-sn-glycero-3-phosphorylcholine (50 mg, 101 µmol), N,N-dimethylaminopyridine (19 mg, 156 µmol), and 1-hydroxybenzotriazole hydrate (11 mg, 78.0 µmol) in CDCl$_3$ (1.6 mL) was treated with 1,3-dicyclohexylcarbodiimide (32 mg, 156 µmol). The reaction was stirred for 2 days. After this time the reaction was treated with additional 1,3-dicyclohexylcarbodiimide (8 mg, 39.0 µmol) and stirred for another 3 days. After this time the reaction was treated with additional 1,3-dicyclohexylcarbodiimide (8 mg, 39.0 mop and stirred for another 2 days. The reaction was treated with additional CDCl$_3$ several times during the course of the reaction to maintain the thinness of the suspension. The reaction was quenched with MeOH and concentrated. The residue was chromatographed on C$_{18}$HS (70%→100% MeOH/water [smooth gradient]) with a Biotage SP1 purification system. The residue from the column fractions was freeze-dried from a mixture of water and t-BuOH to yield 25 mg of protected phospholipopeptide as a white solid.

A mixture of protected phospholipopeptide (24 mg, 18.2 µmol) and 5% palladium on carbon (10 mg) in MeOH (720 µl) and trifluoroacetic acid (80 µL) was stirred under an atmosphere of H$_2$ for 1 day. The reaction mixture was filtered, the filter was rinsed with MeOH, and the filtrate was concentrated. The residue was freeze-dried from a mixture of water and t-BuOH to yield 20 mg of 3.; $^1$H NMR (400 MHz, DMSO-d$_5$) δ 0.84 (t, J=6.4 Hz, 3H), 0.98-1.08 (m, 2H), 1.13-1.35 (m, 48H), 1.41-1.56 (m, 12H), 1.57-1.66 (m, 4H), 1.67-1.75 (m, 2H), 1.82 (s, 3H), 2.23-2.36 (m, 3H), 2.74-2.94 (m, 0H), 3.12 (s, 9H), 3.25-3.35 (m, 5H), 3.53-3.59 (m, 5H), 3.87 (bs, 1H), 4.08-4.36 (m, 8H), 6.65 (dd, J=7.8 Hz, J=3.0 Hz, 2H), 6.93-7.02 (m, 2H), 7.83 (d, J=7.6 Hz, 1H), 7.93-8.00 (m, 1H), 8.11-8.17 (m, 2H), 8.21 (d, J=6.4 Hz, 1H); IR (KBr pellet) 3282, 2927, 1734, 1675, 1629, 1535, 1517, 1205 cm$^{-1}$; HRMS (ESI) C$_{55}$H$_{95}$N$_6$O$_{17}$NaP (M+Na) calculated 1165.6383. found 1165.6396.

Synthesis of 6.

The synthesis of 6 was carried out according to the synthetic scheme of FIG. 2.

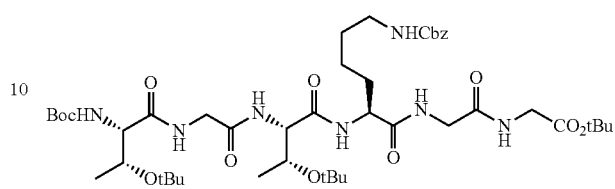

Synthesis of 20:

A. Solid Phase Synthesis—A manual solid phase synthesis was conducted beginning with H-Gly-2ClTrt resin (1 equivalent), (loading-0.4 mmol/g) (5 g, 2.0 mmol), and the following amino acids were coupled (8 equivalents for each coupling): Fmoc-Gly-OH (4.76 g, 16.0 mmol), Fmoc-Lys (Z)—OH (8.04 g, 16.0 mmol), Fmoc-Thr(OtBu)-OH (6.36 g, 16.0 mmol). The amino terminus was capped using di-t-butyl dicarbonate (1 M in THF) (10 mL, 10.0 mmol).

Fmoc Cleavage conditions: the resin was treated with 20% piperidine/DMF for 3 min. Repeated 2 additional times and then washed with DMF.

Coupling conditions: the amino acid (5 equivalents) was dissolved in a 0.5 M solution of 3-(diethoxyphosphoryloxy)-1,2,3-benzotriazin-4(3H)-one (DEPBT) in DMF (5 eq.)(32 mL, 16.0 mmol). Diisopropylethylamine (DIPEA) (10 equivalents) was added to the solution giving an immediate yellow color. This solution was added to the resin containing the free base of the terminal amino acid. The slurry was agitated for the specified time (see the next section). At the end of the reaction time the reagent solution was removed by filtration and the resin washed with DMF.

Coupled in Order:

Gly (coupling time 3 hr), Lys (coupling time 40 min for this and following residues), Thr, Gly, Thr, Boc.

Resin Cleavage:

The resin was treated with acetic acid, trifluoroethanol, and DCM (2:2:6)(40 mL) for 2 hr on a shaker. The solution was then collected by filtration. The cleavage protocol was repeated for 2 more hr on a shaker with a fresh solvent mix and this solution was collected by filtration. The resin was washed with dichloromethane (DCM), all of the washes combined and the solvent was removed in vacuo to give a crude product. The excess acetic acid was removed by dissolving the oil in methanol and toluene and reducing in vacuo. This operation was repeated several times followed by reduction from DCM to give a crude foam (2.68 g) which was carried on to the acid terminus t-butyl ester forming step.

B. t-Butyl ester formation—The peptide was slurried with DCM (20 mL) and ethyl acetate (EtOAc) (10 mL) and t-butyl trichloroacetimidate (2.18 g, 10 mmol) was added. The mixture was refluxed and the peptide slowly went into solution. The reaction was followed by HPLC (Phenomenex C18(2) Reverse Phase Column, 1 mL/min, 80% acetonitrile/water, isocratic, Buffer 0.1% TFA, detection by ELSD and 217 nm DAD, product retention time −5.4 min) When the conversion was complete after 24 hr the solvent was removed in vacuo and the residual oil was dissolved in 80% ACN (Acetonitrileywater (20 mL) and purified by preparative HPLC (Phenomenex C18(2) Reverse Phase Column, 20 mL/min, 80% ACN isocratic, 0.1% TFA, 217 nm). The collected fraction was reduced in vacuo to give 1.4 g (76% yield) of pure 20 as a foam.

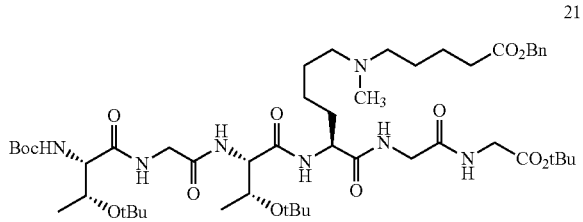 [SMILES: C[C@@H](OC(C)(C)C)[C@H](NC(=O)CNC(=O)[C@@H](NC(=O)OC(C)(C)C)[C@@H](C)OC(C)(C)C)C(=O)N[C@@H](CCCCN(C)CCCCC(=O)OCc1ccccc1)C(=O)NCC(=O)NCC(=O)OC(C)(C)C]

21

Synthesis of 21:

A solution of 20 (2.5 g, 2.7 mmol) in ethanol (60 mL) was added to a slurry of 10% Pd/C (660 mg) in 20 mL of ethanol. Acetic acid (185 µL) was added and the solution was put under a balloon of hydrogen gas for 3 hr. Completion of the Cbz removal was confirmed by HPLC. The catalyst was removed by filtration through a filter disc and the solvent was removed vacuo to give the acetic acid salt of the amine intermediate as a foam (2.07 g, 2.44 mmol, 90% yield). The foam was dissolved in acetonitrile (15 mL) and water (2 mL). Benzyl 5-oxopentanoate (61) (0.654 g, 3.17 mmol, 1.3 eq) was dissolved in acetonitrile and added to the reaction mixture (total volume 20 mL). Acetic acid (0.559 mL, 9.76 mmol, 4 eq) was added next followed by a solution of sodium cyanoborohydride (0.92 g, 14.65 mmol, 6 eq) in 1 of water. The reaction was stirred at room temperature and the pH was checked (pH 5-6). After 1 hr a 37% formaldehyde solution in water (0.5 mL, about 6 mmol) was added and stirring was continued for an additional hour. The reaction solution was made basic with 2N NaOH solution, brine was added and the mixture was extracted with ether for three times. The aqueous layer was next extracted with dichloromethane twice. The combined organic extracts were dried over magnesium sulfate and reduced in vacuo to give 1.13 g of crude product as a white foam. HPLC analysis (Phenomenex C18(2) reverse-phase column, 50 to 90% acetonitrile/water over 10 min, buffer 0.1% trifluoroacetic acid, product retention time-7.25 min) indicated that 79% of the crude material was the desired product. The crude product was dissolved in 50% ACN/water with 0.1% TFA (20 mL) and trifluoroacetic acid (181 µL) was added to protonate the amine. Purification over a preparative C18 reverse-phase column, using the same conditions as used for the analytical runs, and lyophilization gave 21 (1.24 g, 46% yield) as a white solid. $^1$H NMR (400 MHz, DMSO-$d_6$) δ 0.99 (d, 3H), 1.02 (d, 3H), 1.10 (s, 9H), 1.13 (s, 9H), 1.20-1.35 (m, 4H), 1.39 (s, 18H), 1.52-1.67 (m, 5H), 1.67-1.79 (m, 1H), 2.43 (t, 2H), 2.70 (d, 3H), 2.87-3.15 (m, 4H), 3.75 (m, 4H), 3.83 (m, 2H), 3.88 (m, 2H), 3.96 (m, 1H), 4.30-4.36 (m, 2H), 5.10 (s, 2H), 7.30-7.40 (m, 5H), 7.75 (d, 1H), 7.97 (d, 1H), 8.07 (t, 1H), 8.14-8.21 (m, 2H), 9.33 (br s, 1H); $^{13}$C NMR (400 MHz, DMSO-$d_6$) δ 19.2, 20.1, 21.8, 23.2, 28.1, 28.3, 28.4, 31.9, 33.2, 41.6, 41.9, 42.6, 52.6, 54.9, 55.2, 57.6, 59.5, 65.9, 67.6, 68.0, 74.0, 74.4, 78.8, 81.1, 128.4, 128.5, 128.9, 136.6, 155.5, 158.4, 158.8, 168.9, 169.2, 169.3, 169.5, 170.65, 171.7, 172.8; HRMS (ESI) $C_{50}H_{86}N_7O_{13}$ (M+H$^+$) calculated 992.6284. found 992.6251.

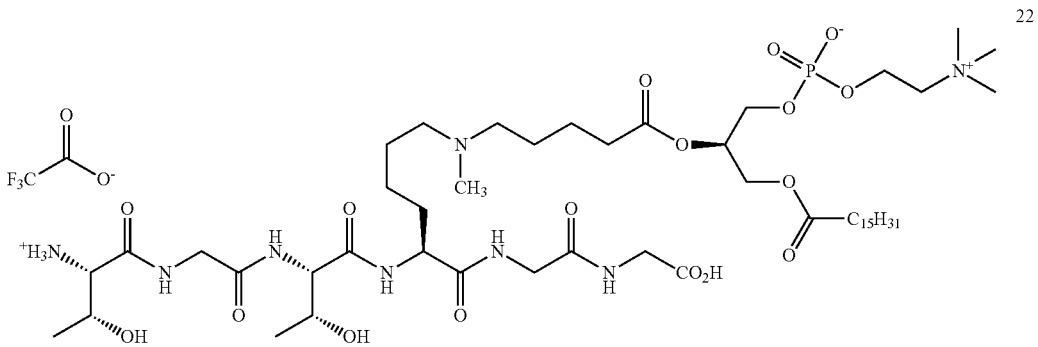

22

Synthesis of 22:

A catalyst slurry was formed by placing 370 mg of 10% Pd/C in a dry flask and adding ethanol (3 mL). A solution of 21 (1.24 g, 1.121 mmol) in ethanol (15 mL) was added to the slurry and the mixture was put under a balloon of hydrogen for 3 hr. An aliquot was checked by HPLC (Phenomenex C18(2) reverse-phase column, 50 to 90% acetonitrile/water over 15 min, buffer 0.1% trifluoroacetic acid, product retention time-4.6 min) and showed complete conversion to product. The catalyst was removed by filtration and the solution was reduced in vacua to give 1.07 g (94% yield) of the acid as a foam/oil. (HRMS (ESI) $C_{43}H_{80}N_7O_{13}$ (M+H$^+$) calc 902.5814. found 902.5836).

The acid (1.07 g, 1.053 mmol, 1 eq) and lyso-PC (1.566 g, 3.16 mmol, 3 eq) were dissolved in toluene with sonication in the reaction flask. The solvent was removed in vacua to eliminate any residual ethanol twice. The flask was put under high vacuum using a vacuum pump for 2 days to complete solvent removal. The solid was slurried in ethanol-free chloroform (40 mL) and diisopropyl carbodiimide (DIC) (0.326 mL, 2.1 mmol, 2 eq) was added followed by DMAP (257 mg, 2.1 mmol, 2 eq). Glass beads were added to just below the solvent surface and the reaction flask was sonicated for 2 hr. The solution was pipetted away from the glass beads and the beads washed with additional chloroform. The combined solutions were reduced in vacuo to give 4.24 g of crude product. HPLC (Phenomenex C18(2) reverse-phase column, 50-90% acetonitrile/water over 10 min, buffer 0.1% trifluoroacetic acid, product retention Lime-13.8 min) showed complete conversion to product. The material was dissolved in 50% acetonitrile/water and purified by HPLC (Phenomenex C18(2) reverse-phase column, 10 micron, 250×30 mm, 40 mL/min, 60 to 90% acetonitrile/water over 15 min, buffer 0.1% TFA). The product fraction was partially reduced in vacuo, to remove most of the acetonitrile and lyophilized. The lyophilate was collected in dichloromethane, and reduced again to give the product oil. Drying overnight under high vacuum gave 1.07 g (68% yield) of the coupled product. This material was dissolved in trifluoroacetic acid (5 mL) and stirred in an ice bath for 2.5 hr. The solvent was removed in vacuo, the residue dissolved in dichloromethane, and reduced in vacuo to give a product oil. HPLC (Phenomenex C18(2) reverse-phase column, 30% acetonitrile/water for 2 min, then to 90% acetonitrile at 10 min, buffer 0.1% trifluoroacetic acid, product retention time-9.59 min (98% pure)) The oil was dissolved in water and lyophilized to give 846.2 mg (88% yield) of 22 as a white solid. $^1$H NMR (400 MHz, DMSO-d6) δ 0.85 (t, 3H), 1.04 (d, 3H), 1.19 (d, 3H), 1.19-1.80 (m, 34H), 2.28 (t, 2H), 2.30-2.45 (m, 2H), 2.66 (d, 3H), 2.80-3.08 (m, 5H), 3.13 (s, 9H), 3.57 (s, 2H), 3.62 (br s, 1H), 3.75 (m, 4H), 3.80-4.05 (m, 7H), 4.10-4.35 (m, 7H), 5.18 (s, 1H), 5.5 (br s, 1H), 8.01 (m, 2H), 8.05-8.20 (m, 4H), 8.32 (m, 1H), 8.83 (t, 1H), 10.80 (s, 1H); $^{13}$C NMR (400 MHz, DMSO-d6) δ 14.4, 20.1, 20.2, 22.5, 22.9, 23.2, 24.8, 28.8, 29.1, 29.3, 29.4, 29.5, 31.7, 33.7, 41.0, 42.1, 42.3, 53.5, 58.6, 59.3, 62.4, 64.0, 65.6, 66.3, 67.0, 70.8, 158.3, 158.6, 167.6, 168.9, 169.4, 170.3, 171.5, 172.1, 173.1; HRMS (ESI) $C_{50}H_{96}N_8O_{17}P$ (M+H$^+$) calculated 1111.6631. found 1111.6614.

41.1, 42.2, 42.7, 52.8, 53.6, 55.3, 58.6, 59.7, 59.4, 62.5, 63.9, 65.8, 66.8, 67.2, 71.0, 169.4, 169.6, 170.5, 170.6, 171.4, 171.6, 172.1, 172.4, 173.1; HRMS (ESI) $C_{52}H_{98}N_8O_{18}P$ (M+H$^+$) calculated 1153.6737. found 1153.6749.

Synthesis of Compounds 23-27.

Figure 6:
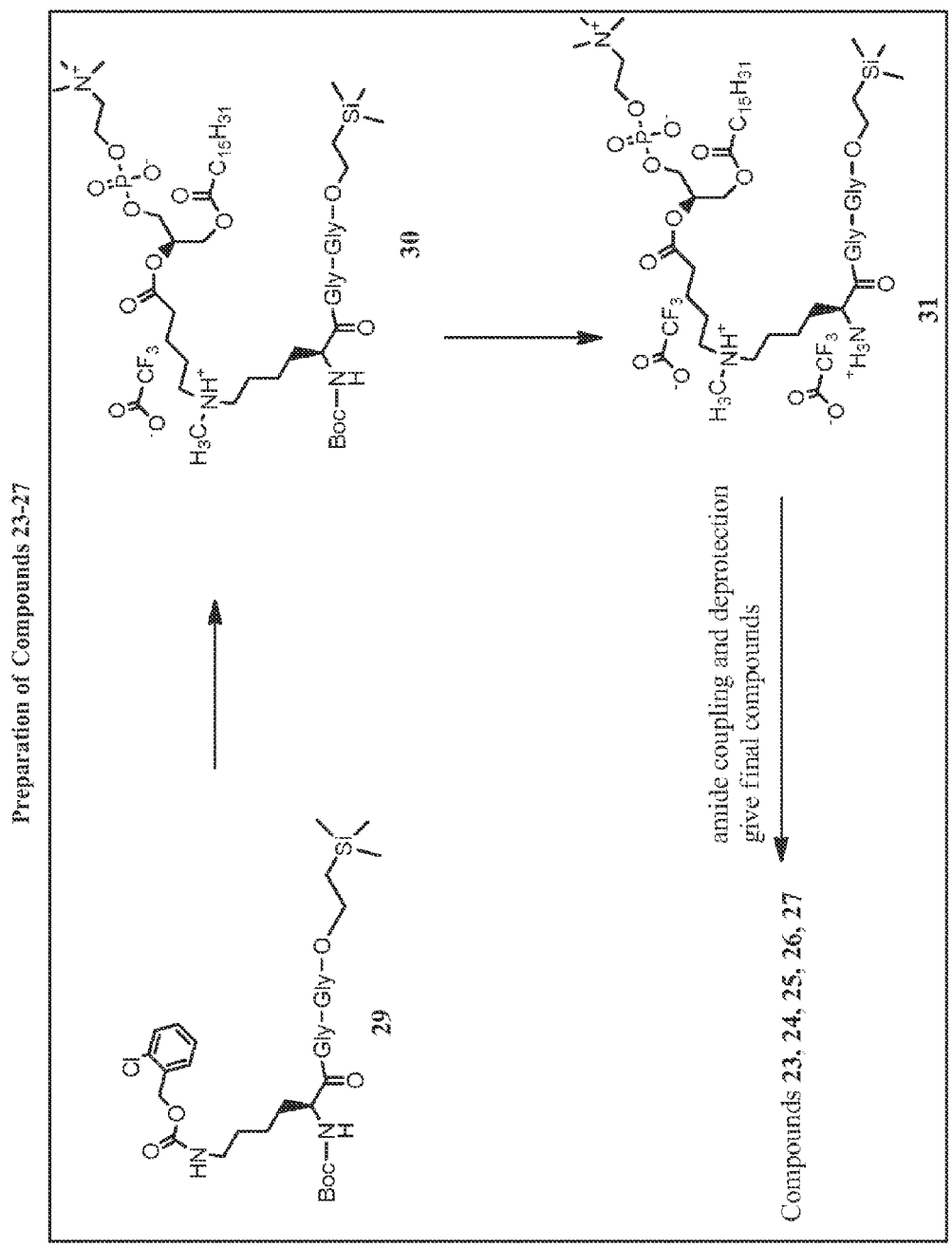
FIG. 6 illustrates a synthetic scheme for the synthesis of compounds 23-27.

Compounds 23-27 were synthesized according to the scheme illustrated in FIG. 6.

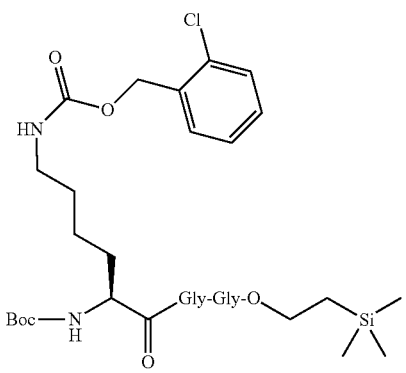

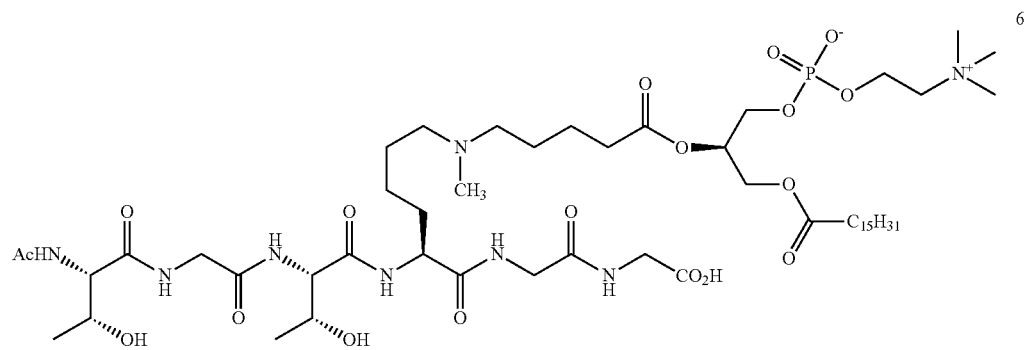

Synthesis of 6.

Compound 22 (49.8 mg, 0.037 mmol, 1 eq) was dissolved in 2 mL of anhydrous dichloromethane. 1-Acetylimidazole (6.1 mg, 0.056 mmol, 1.5 eq) and DIPEA (25.9 μL, 0.149 mmol, 4 eq) were added and the reaction was stirred for 18 hr. Complete conversion to product was seen when the reaction was checked by HPLC (Phenomenex C18(2) reverse-phase column, 30 to 90% acetonitrile/water over 10 min, buffer 0.1% TFA, product retention time-9.3 min). The solvent was removed in vacuo and the residual oil was dissolved in 50% acetonitrile/water and purified over a preparative HPLC column using the same conditions as for the analytical HPLC. The pure fraction was lyophilized overnight. The sample was re-lyophilized from water to give 25.6 mg (60% yield) of 6 as a white solid. $^1$H NMR (400 MHz, DMSO-d$_6$) δ 0.71, (t, 3H), 0.89 (d, 3H), 0.92 (d, 3H), 1.05-1.70 (m, 34H), 1.78 (s, 3H), 2.10-2.20 (m, 3H), 2.25-2.40 (m, 6H), 2.80 (s, 4H), 2.99 (s, 9H), 3.42 (s, 3H), 3.54-3.70 (m, 7H), 3.70-3.90 (m, 4H), 3.95-4.05 (m, 4H), 4.05-4.15 (4H), 4.90 (br s, 1H), 5.05 (s, 1H), 7.62 (d, 1H), 7.84 (d, 1H), 7.93 (s, 2H), 8.09 (t, 1H), 8.16 (s, 1H); $^{13}$C NMR (400 MHz, DMSO-d$_6$) δ 14.4, 20.0, 20.2, 22.5, 22.9, 23.2, 24.8, 28.8, 29.1, 29.3, 29.4, 29.5, 31.4, 31.7, 33.7, 33.8, Synthesis of 29.

A. Solid Phase Synthesis—A manual solid phase synthesis was conducted using the same procedure previously described for 20 beginning with H-Gly-2ClTrt resin. (loading-0.71 mmol/g) (2.0 g, 1.42 mmol), and the following amino acids were coupled (8 eq. for each coupling): Fmoc-Gly-OH (2.11 g, 7.1 mmol) and Boc-Lys(2-Cl Z)—OH (2.95 g, 7.1 mmol). The procedure gave a crude foam (497.6 mg) which was carried on to the acid terminus ester forming step.

B. 2-Trimethylsilylethyl ester formation. The peptide was dissolved in DCM (10 mL) and EDC (360 mg, 1.88 mmol), 2-trimethylsilyl ethanol (0.202 mL, 1.41 mmol) and DMAP (11.5 mg, 0.09 mmol) were added with stirring. After 18 hr the solution was extracted with 1N HCl solution. The organic layer was then extracted with saturated sodium bicarbonate solution and reduced in vacuo. The residual oil was solubilized in 50% acetonitrile/water and purified by HPLC (70% ACN/water, 0.1% TFA, 217 nm). The collected fraction was reduced in vacuo to give 150 mg (25% yield) of pure 29 as a clear oil. Accurate APCI MS: Found 629.2777; Calculated 629.2773 for $C_{28}H_{46}N_4O_8SiCl$ (M+H$^+$),

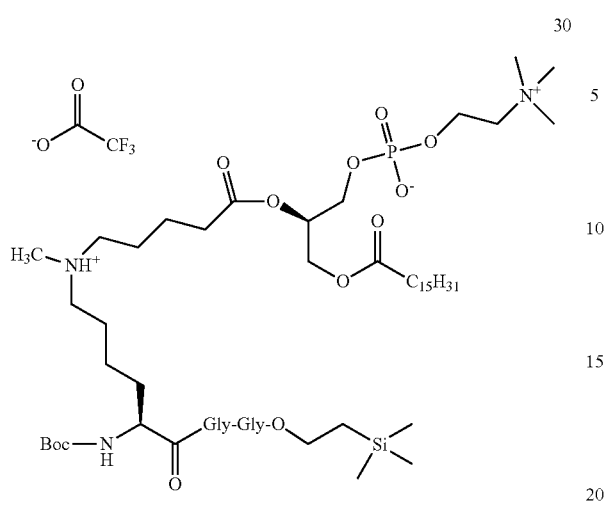

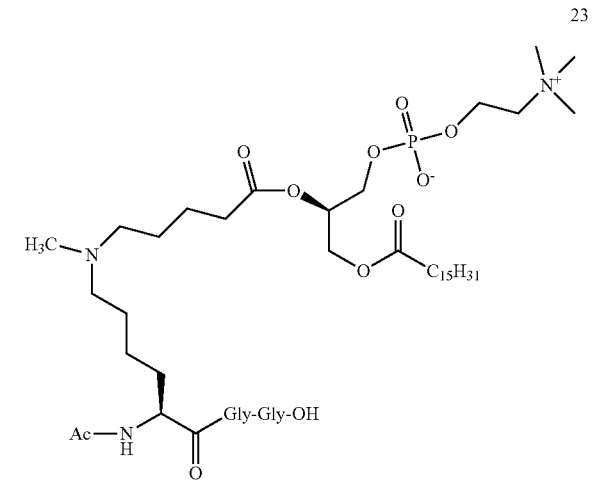

Synthesis of 30.

Compound 29 (149 mg, 0.237 mmol) was converted to 30 by the method previously described for preparing 21. HPLC purification (Phenomenex C18(2) Reverse Phase Column, 20 mL/min, 50 to 90% acetonitrile/water, over 10 min, Buffer 0.1% TFA, detection by ELSD and 217 nm DAD, product retention time-12.1 min) gave 220 mg of 30 containing some lyso-PC starting material which would be removed in the subsequent step.

Synthesis of 23.

Compound 31 (12.5 mg, 0.012 mmol, 1 eq) was dissolved in 1 mL of anhydrous dichloromethane. 1-Acetylimidazole (1.9 mg, 0.017 mmol, 1.5 eq) and diisopropylethylamine (8.06 µL, 0.046 mmol, 4 eq) were added and the reaction was stirred for 18 hr. Complete conversion to product was seen when the reaction was checked by HPLC (Phenomenex C18(2) Reverse Phase Column, 1 mL/min, 50 to 90% acetonitrile/water, over 10 min, Buffer 0.1% TFA, detection by ELSD and 217 nm DAD). The solvent was removed in vacua and the residual oil was dissolved in 50% TFA/DCM (2 mL). This solution was kept at 0° C. overnight. The solvent was removed in vacua and the residual oil was purified over a preparative HPLC column using the same conditions as for the analytical HPLC (retention time 6.83 min). The pure fraction was lyophilized to give 7.4 mg (71% yield) of pure 23 as a white solid. Accurate ESI MS: Found 894.5558. Calculated 894.5569 for $C_{42}H_{81}N_5O_{13}P$ (M+H$^+$).

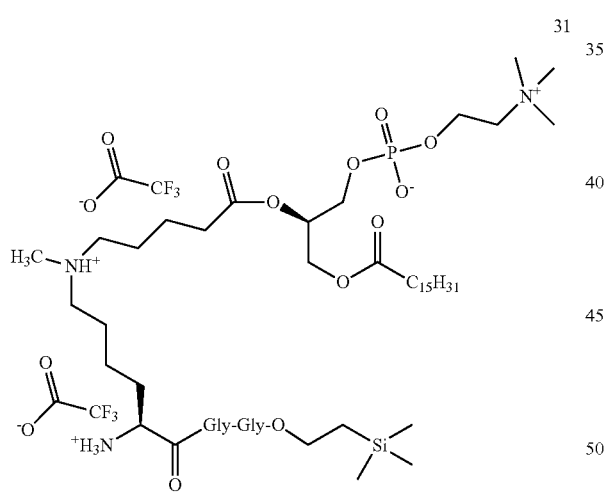

Synthesis of 31.

Compound 30 was dissolved in 50% trifluoroacetic acid/DCM (4 mL) and stirred in an ice bath for 10 min. The solvent was removed in vacuo, the residue dissolved in dichloromethane, and reduced in vacuo to give a product oil. HPLC (Phenomenex C18(2) Reverse Phase Column, 1 mL/min, 50 to 90% acetonitrile/water over 10 min. Buffer 0.1% TFA, detection by ELSD and 217 nm DAD, product retention time-8.27 min). The oil was dissolved in 50% ACN/water and purified by preparative HPLC using the same conditions as the analytical run. The pure fraction was lyophilized to give 71.1 mg (28% yield over 2 steps) of 31 as a white solid. ESI MS: 952.6 (M+H$^+$).

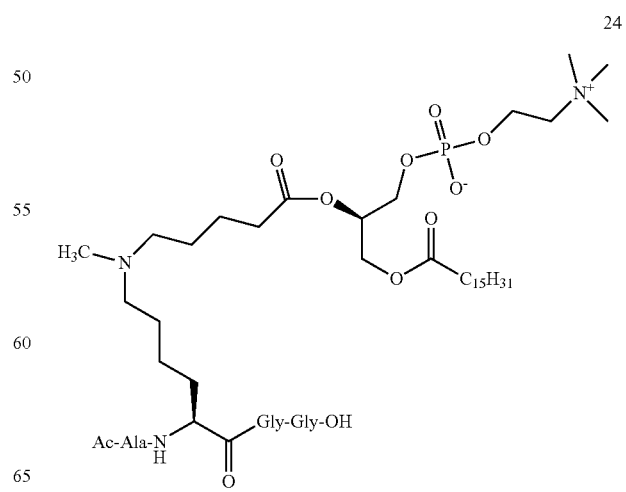

Synthesis of 24.

Compound 31 (15.9 mg, 0.013 mmol, 1 eq) was dissolved in 1 of anhydrous DMF along with Boc-Ala-OH (10.2 mg, 0.054 mmol, 4 eg), DEPBT (16.12 mg, 0.054 mmol, 4 eg), and DIPEA (18.77 μL, 0.108 mmol, 8 eq). After 4 hr it was reduced in vacua and solubilized in 50% ACN/water, HPLC (Phenomenex C18(2) Reverse Phase Column, 1 mL/min, 50 to 90% acetonitrile/water. over 10 min, Buffer 0.1% TFA, detection by ELSD and 217 nm DAD) showed a product peak at 11.56 min. The product was purified by HPLC using the same system. The pure product fraction was reduced in vacua to give 16.4 mg of a clear oil. The oil was dissolved in 50% TFA/DCM (2 mL). This solution was kept at 0° C. overnight. The solvent was removed in vacua giving an oil, HPLC showed complete conversion to the di-deprotected compound (HPLC ret. time-4.62 min). This compound was mixed with 1-acetylimidazole (2.18 mg, 0.020 mmol, 1.5 eq) and DIPEA (9.23 μL, 0.053 mmol, 4 eq) and stirred overnight at room temperature. The solvent was removed in vacuo and the residual oil was purified over a preparative HPLC column using the same conditions as for the previous analytical HPLC (retention time 6.69 min). The pure fraction was lyophilized to give 5.6 mg (44% yield) of 24 as a white solid. MALDI MS: 965.502 (M+H$^+$).

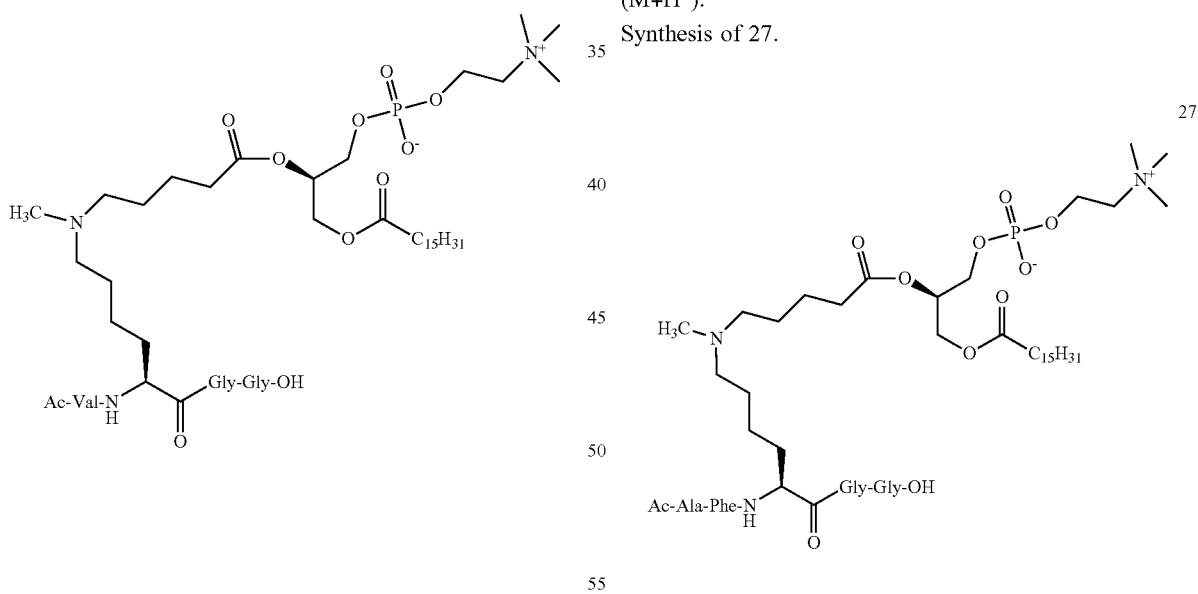

Synthesis of 25.

Compound 31 (21.0 mg, 0.018 mmol, 1 eq) was dissolved in 1 mL of anhydrous DMF along with Boc-Val-OH (15.46 mg, 0.054 mmol, 4 eq), DEPBT (21.29 mg, 0.054 mmol, 4 eq), and DIPEA (24.79 μL, 0.108 mmol, 8 eq). The same procedure used for 24 gave pure 25 (8.1 mg, 52% yield) as a white solid. HPLC ret. time 7.17 min. Accurate ESI MS: Found 993.6237. Calculated 993.6253 for $C_{47}H_{90}N_6O_{14}P$ (M+H$^+$).

Synthesis of 26.

Compound 31 (17.6 mg, 0.015 mmol, 1 eq) was dissolved in 1 mL of anhydrous DMF along with Boc-Phe-OH (15.82 mg, 0.060 mmol, 4 eq), DEPBT (17.85 mg, 0.060 mmol, 4 eq), and DIPEA (20.78 μL, 0.119 mmol, 8 eq). The same procedure used for 24 gave pure 26 (6.9 mg, 48% yield) as a white solid. HPLC ret. time 8.01 min. Accurate ESI MS: Found 1041.6299. Calculated 1041.6253 for $C_{51}H_{90}N_6O_{14}P$ (M+H$^+$).

Synthesis of 27.

Synthesis of 27.

Compound 31 (14.9 mg, 0.013 mmol, 1 eq) was dissolved in 1 mL of anhydrous DMF along with Boc-Ala-Phe-OH (16.99 mg, 0.050 mmol, 4 eq), DEPBT (15.11 mg, 0.050 mmol, 4 eq), and DIPEA (17.59 μL, 0.101 mmol, 8 eg). The same procedure used for 24 gave pure 27 (4.7 mg, 34% yield) as a white solid. HPLC ret. time 7.70 min. Accurate ESI MS: Found 1112.6604. Calculated 1112.6624 for $C_{54}H_{95}N_7O_{15}P$ (M+H$^+$).

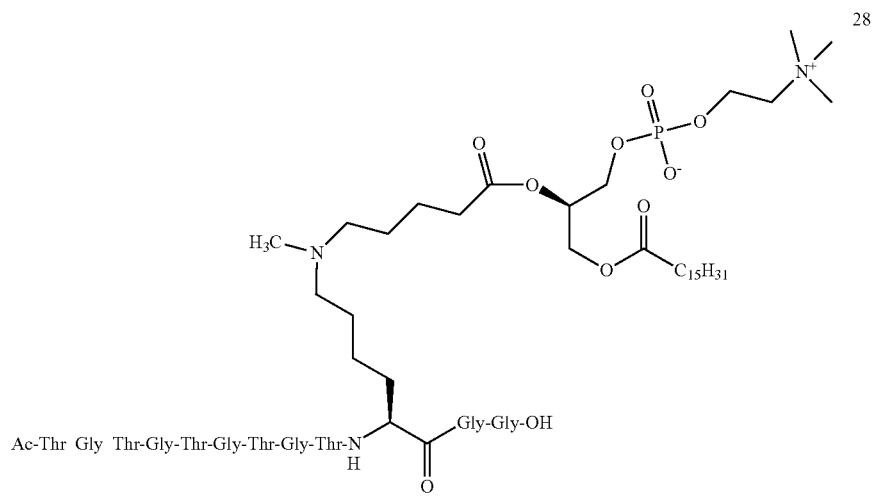

Synthesis of 28.

A solution of AcT(OtBu)GT(OtBu)GT(OtBL)G-OH (22.9 mg, 0.033 mmol, prepared by manual solid phase synthesis) in DMF (1 mL) was treated with 1,1'-carbonyldiimidazole (5.29 mg, 0.033 mmol) and the solution was stirred at room temperature for 4 hr. Separately, 22 (20 mg, 0.016 mmol) was dissolved in DMF (1 mL) and DIPEA (11.37 µL, 0.065 mmol) was added. The two DMF solutions were mixed and the resulting solution was stirred for 18 hr. The solvent was removed in vacuo and the residual oil was dissolved in 90% ACN/water and analyzed by HPLC (Phenomenex C18(2) Reverse Phase Column, 1 mL/min, 30% acetonitrile/water for 2 min then to 90% ACN, Buffer 0.1% TFA, detection by ELSD and 217 nm DAD) showing a product peak at 11.6 min. Purification by HPLC using the same conditions and removal of solvent in vacuo gave 13.1 mg of product. ESI MS 898.7 ((M+H)/2 for doubly charged ion). The protecting groups were removed by treatment with TFA (2 mL) for 2 hr at 0° C. The reaction was reduced in vacuo and dissolved in 50% ACN/water. HPLC showed a product peak at 9.95 min (more than 90% pure). The solution was lyophilized to give 9.6 mg of 28 as a white solid. Accurate ESI MS: Found 1627.8788. Calculated 1627.8811 for $C_{70}H_{128}N_{14}O_{27}P$ (M+H$^+$).

CD36 Macrophage Receptor Binding Competition Assay.

Binding of biotinylated OxLDL ligands to murine macrophages plated in microtiter wells was assessed by a chemiluminescent binding assay. Isolated human LDL was biotinylated according to manufacturer's protocol (Catalog No. 21326; Pierce Biotechnology). Native and biotinylated native LDL were subjected to copper sulfate oxidation in parallel to prepare unlabelled and biotinylated CuOxLDL ligands, respectively. It has been previously shown that CuOxLDL contains approximately 78 moles of PC-epitopes per mole of apoB-100 (the sole protein on LDL). The biotinylated native LDL and CuOxLDL ligands of equal protein concentration were serially diluted and tested for binding to adherent macrophages. The specificity of the binding of biotinylated CuOxLDL to macrophages was tested in competition experiments, where fixed concentrations of biotinylated CuOxLDL were incubated with the serially diluted competitor and controls in PBS. The ligand-competitor solutions were incubated overnight at 4° C. Murine macrophages from the J774 cell line were cultured in 10% fetal bovine serum in DMEM (DMEM-10) and plated in 100 µL L929-fibroblast conditioned media at 100,000 or 25,000 cells/well, respectively, in sterile 96-well flat-bottom white plates (Greiner Bio-One). The plating media consisted of 20% L929-fibroblast conditioned DMEM-10 and 80% fresh DMEM-10 and served as a source of growth factors, including macrophage colony-stimulating factor. After 72 hours, the plates were washed gently 5 times with PBS using a microtiter plate washer (Dynex Technologies, Chantilly, Va.), and wells were blocked with ice-cold 200 µL DMEM for 30 min, while plates were kept on ice. After washing, macrophages were incubated with ice-cold ligand and ligand-competitor solutions (100 µL/well) for 2 hours on ice, washed again, and fixed with ice-cold 3.7% formaldehyde in PBS for 30 min in the dark. After fixing the macrophages, the remaining part of the assay was carried out at room temperature. Macrophage-bound biotinylated OxLDL ligands were detected with NeutrAvidin-conjugated alkaline phosphatase (Pierce Biotechnology), LumiPhos 530 (Lumigen, Southfield, Mich.), and a Dynex Luminometer (Dynex Technologies). Ligand binding was recorded and expressed as relative light units counted per 100 milliseconds (RLU/100 ms) or in the case of inhibition of binding by competitors as a ratio of binding in the presence of competitor (B) divided by binding in the absence of competitor ($B_0$), The $IC_{50}$ value of each competitor was calculated by standard methods.

REFERENCES (1) Steinberg, D.; Parthasarathy, S.; Carew, T. E.; Khoo, J. C.; Witztum, J. L. Beyond Cholesterol. Modifications of Low-Density Lipoprotein that Increase its Atherogenicity. N. Engl. J. Med. 1989, 320, 915-924.

(2) Witztum, J. L.; Steinberg, D. Role of Oxidized Low Density Lipoprotein in Atherogenesis J. Clin. Invest. 1991, 88, 1785-1792.

(3) Krieger, M. The Other Side of Scavenger Receptors: Pattern Recognition for Host Defense. Curr. Opin. Lipidol. 1997, 8, 275-280.

(4) Sawamura, T.; Kume, N.; Aoyama, T.; Moriwaki, H.; Hoshikawa, H.; Aiba, Y.; Tanaka, T.; Miwa, S.; Katsura, Y.; Kita, T.; Masaki, T. An Endothelial Receptor for Oxidized Low-Density Lipoprotein. Nature (London, U.K.) 1997, 386, 73-77.

(5) Steinberg, D. Low Density Lipoprotein Oxidation and its Pathobiological Significance. J. Biol. Chem, 1997, 272, 20963-20966.
(6) Yamada, Y.; Doi, T.; Hamakubo, T.; Kodama, T. Scavenger Receptor Family Proteins. Roles for Atherosclerosis, Host Defense, and Disorders of the Central Nervous System. Cell. Mol. Life Sci. 1998, 54, 628-640
(7) Endemann, G.; Stanton, L. W.; Madden, K. S.; Bryant, C. M.; White, R. T.; Protter, A. A. CD36 is a Receptor for Oxidized Low Density Lipoprotein. Journal of Biological Chemistry J. Biol. Chem. 1993, 268, 11811-11816.
(8) McIntyre, T. M.; Zimmerman, G. A.; Prescott, S. M. Biologically Active Oxidized Phospholipids. J. Biol. Chem. 1999, 274, 25189-25192.
(9) Witztum, J. L.; Berliner, J. A. Oxidized Phospholipids and Isoprostanes in Atherosclerosis. Curr. Opin. Lipidol. 1998, 9, 441-448.
(10) Gillotte, K. L.; Horkko, S.; Witztum, J. L.; Steinberg, D. Oxidized Phospholipids, Linked to Apolipoprotein B of Oxidized LDL, are Ligands for Macrophage Scavenger Receptors. J. Lipid Res. 2000, 41, 824-833.
(11) Kamido, H.; Kuksis, A.; Marai, L.; Myher, J. J. Identification of Core Aldehydes Among In Vitro Peroxidation Products of Cholesteryl Esters. Lipids 1993, 28, 331-336.
(12) Kamido, H.; Kuksis, A.; Marai, L; Myher, J. J. Lipid Ester-Bound Aldehydes among Copper-Catalyzed Peroxidation Products of Human Plasma Lipoproteins. J. Lipid Res. 1995, 36, 1876-1886.
(13) Boullier, A.; Gillotte, K. L.; Horkko, S.; Green, S. R.; Friedman, P.; Dennis, E. A.; Witztum, J. L.; Steinberg, D.; Quehenberger, O. The Binding of Oxidized Low Density Lipoprotein to Mouse CD36 is Mediated In Part by Oxidized Phospholipids That are Associated with Both the Lipid and Protein Moieties of the Lipoprotein. J. Biol. Chem. 2000, 275, 9163-9169.
(14) Podrez, E. A.; Poliakov, E.; Shen, Z.; Zhang, R.; Deng, Y.; Sun, M.; Finton, P. J.; Shan, L.; Febbraio, M.; Hajjar, D. P.; Silverstein, R. L.; Hoff, H. F.; Salomon, R. G.; Hazen, S. L. A Novel Family of Atherogenic Oxidized Phospholipids Promotes Macrophage Foam Cell Formation via the Scavenger Receptor CD36 and is Enriched in Atherosclerotic Lesions. J. Biol. Chem. 2002, 277, 38517-38523.
(15) Podrez, E. A.; Poliakov, E.; Shen, Z.; Zhang, R.; Deng, Y.; Sun, M.; Finton, P. J.; Shan, L.; Gugiu, B.; Fox, P. L.; Hoff, H. F.; Salomon, R. G.; Hazen, S. L. Identification of a Novel Family of Oxidized Phospholipids That Serve as Ligands for the Macrophage Scavenger Receptor CD36. J. Biol. Chem. 2002, 277, 38503-38516.
(16) Horkko, S.; Bird, D. A.; Miller, E.; Itabe, H.; Leitinger, N.; Subbanagounder, G.; Berliner, J. A.; Friedman, P.; Dennis, E. A.; Curtiss, L. K.; Palinski, W.; Witztum, J. L. Monoclonal Autoantibodies Specific for Oxidized Phospholipids or Oxidized Phospholipid-Protein Adducts Inhibit Macrophage Uptake of Oxidized Low-Density Lipoproteins, J. Clin. Invest. 1999, 103, 117-128.
(17) Friedman, P.; Horkko, S.; Steinberg, D.; Witztum, J. L.; Dennis, E. A. Correlation of Antiphospholipid Antibody Recognition with the Structure of Synthetic Oxidized Phospholipids. Importance of Schiff Base Formation and Aldol Condensation. J. Biol, Chem, 2002, 277, 7010-7020.
(18) Boullier, A.; Friedman, P.; Harkewicz, R.; Hartvigsen, K.; Green, S. R.; Almazan, F.; Dennis, E. A.; Steinberg, D.; Witztum, J. L.; Quehenberger, O. Phosphocholine as a Pattern Recognition Ligand for CD36. J. Lip. Res., 2005, 46, 969-976.
(19) Rosseto, R.; Hajdu, J. A Rapid and Efficient Method for Migration-Free Acylation of Lysophospholipids: Synthesis of Phosphatidylcholines with sn-2-Chain-Terminal Reporter Groups. Tetrahedron Lett. 2005, 46, 2941-2944.
(20) Binder, C. J.; Horrko, S.; Dewan, A.; Chang, M.-K.; Kieu, E. R; Goodyear, C. S.; Shaw, P. X.; Palinski, W.; Witztum, J. L.; Silverman, G. J. Pneumococcal Vaccination Decreases Atherosclerotic Lesion Formation: Molecular Mimicry Between *Streptococcus pneumoniae* and Oxidized LDL. Nat. Med. 2003, 9, 736-743.
(21) Chou, M.-Y.; Foglestrand, L.; Hartvigsen, K.; Hansen, L. F.; Woelkers, D.; Shaw, P. X.; Choi, J.; Perkmann, T.; Backhed, F.; Miller, Y. I.; Horkko, S.; Corr, M.; Witztum, J. L.; Binder, C. J. Oxidation-Specific Epitopes are Dominant Targets of Innate Natural Antibodies in Mice and Humans. J. Clin. Invest. 2009, 119, 1335-1349.
(22) Fields et al. Pept. Res. 1991 4, 95-101.

The invention claimed is:

1. A peptide-phospholipid conjugate of Formula 1:

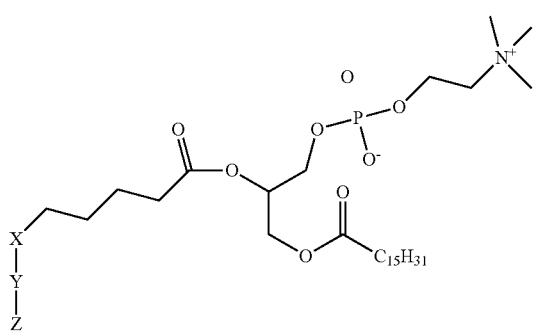

Formula 1 wherein:
X is selected from the group consisting of —CR$^1$R$^2$—, —NR$^3$—, —O—, —S—, and —S$^+$(R$^3$)—;
Y is selected from the group consisting of a bond, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl;
Z is a peptide comprising 1 to 50 amino acids;
R$^1$ and R$^2$ are each independently selected from the group consisting of alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl; and
R$^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

2. The peptide-phospholipid conjugate of claim 1, wherein X is an —NR$^3$— group, wherein R$^3$ is selected from the group consisting of alkyl, alkenyl, alkynyl, haloalkyl, alkoxyalkyl, hydroxyalkyl, aminoalkyl, amino, and ether.

3. The peptide-phospholipid conjugate of claim 1, wherein X is an —NR$^3$— group, wherein R$^3$ is selected from the group consisting of alkyl, haloalkyl, alkoxyalkyl, hydroxyalkyl, and aminoalkyl.

4. The peptide-phospholipid conjugate of claim 1, wherein Y is selected from the group consisting of a bond, alkyl, alkenyl, alkynyl, haloalkyl, alkoxyalkyl, and hydroxyalkyl.

5. The peptide-phospholipid conjugate of claim 1, wherein Y is selected from the group consisting of a bond and alkyl.

6. The peptide-phospholipid conjugate of claim 1, wherein Z is a peptide comprising 1 to 25 amino acids.

7. The peptide-phospholipid conjugate of claim 1, wherein Z is a peptide comprising 1 to 15 amino acids.

8. A method of manufacturing a peptide-phospholipid conjugate of Formula 2:

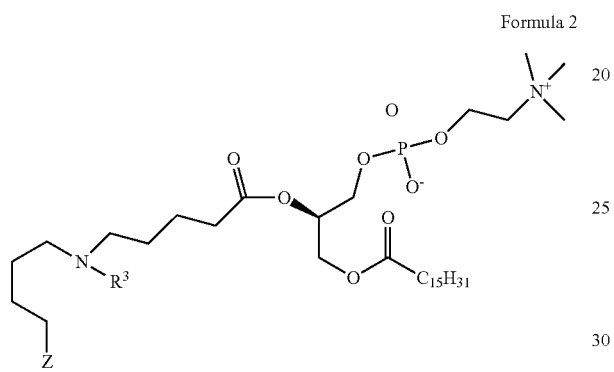

Formula 2 the method comprising forming a mixture comprising an acid of Formula 3 and lyso-PC:

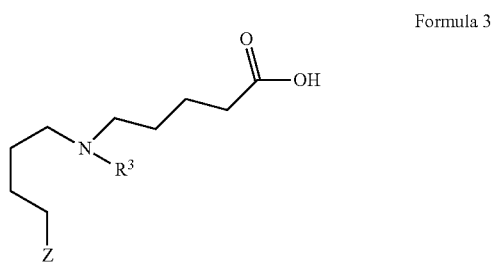

Formula 3 wherein:
R$^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl; and
Z is a peptide comprising 1 to 50 amino acids.

9. The method of claim 8, wherein R$^3$ is selected from the group consisting of alkyl, haloalkyl, alkoxyalkyl, hydroxyalkyl, and aminoalkyl.

10. The method of claim 8, wherein R$^3$ is alkyl.

11. The method of claim 8, wherein Z is a peptide comprising 1 to 25 amino acids.

12. The method of claim 8, wherein Z is a peptide comprising 1 to 15 amino acids.

13. The method of claim 8, wherein the mixture further comprises a coupling reagent.

14. The method of claim 13, wherein the coupling reagent is a carbodiimide.

15. The method of claim 13, wherein the coupling reagent is selected from the group consisting of dicyclohexylcarbodiimide, diisopropylcarbodiimide, and combinations thereof.

16. The method of claim 13, wherein the mixture further comprises a solvent selected from the group consisting of CHCl$_3$, CH$_2$Cl$_2$, tetrahydrofuran, acetonitrile, dimethylformamide, and mixtures thereof.

17. A pharmaceutical formulation for treating atherosclerosis, the formulation comprising: a peptide-phospholipid conjugate of Formula 1 or a pharmaceutically acceptable salt, prodrug, salt of a prodrug, or a combination thereof, and a pharmaceutically acceptable excipient:

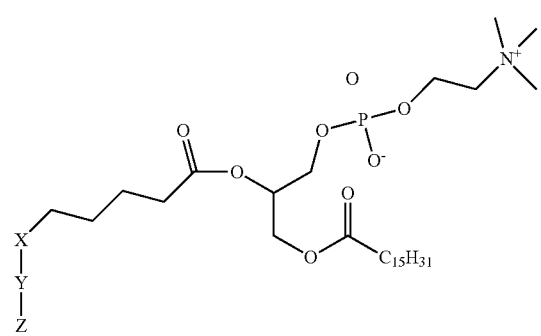

Formula 1 wherein:
X is selected from the group consisting of —CR$^1$R$^2$—, —NR$^3$—, —O—, —S—, and —S$^+$(R$^3$)—;
Y is selected from the group consisting of a bond, alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl;
Z is a peptide comprising 1 to 50 amino acids;
R$^1$ and R$^2$ are each independently selected from the group consisting of alkyl, alkenyl, alkynyl, haloalkyl, alkoxyalkyl, hydroxyalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl; and
R$^3$ is selected from the group consisting of alkyl, alkenyl, alkynyl, haloalkyl, alkoxyalkyl, hydroxyalkyl, aminoalkyl, amino, ether, cycloamino, cycloether, aryl, heteroaryl, arylalkyl, heteroarylalkyl, hydroxyaryl, arylether, cycloalkyl, heterocycloalkyl, hydroxycycloalkyl, halocycloalkyl, and aminocycloalkyl.

18. The pharmaceutical formulation of claim 17, wherein moiety X is an —NR$^3$— group, wherein R$^3$ is selected from the group consisting of alkyl, haloalkyl, alkoxyalkyl, hydroxyalkyl, and aminoalkyl.

19. The pharmaceutical formulation of claim 18, wherein R$^3$ is alkyl.

20. The pharmaceutical formulation of claim 17, wherein moiety Y is selected from the group consisting of a bond and alkyl.

* * * * *